US010016264B2

(12) United States Patent
Otsuka et al.

(10) Patent No.: US 10,016,264 B2
(45) Date of Patent: Jul. 10, 2018

(54) TEETH BLEACHING APPARATUS

(71) Applicant: Panasonic Intellectual Property Management Co., Ltd., Osaka (JP)

(72) Inventors: Risa Otsuka, Kyoto (JP); Masayoshi Nagayama, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 15/121,254

(22) PCT Filed: May 25, 2015

(86) PCT No.: PCT/JP2015/002608
§ 371 (c)(1),
(2) Date: Aug. 24, 2016

(87) PCT Pub. No.: WO2015/186307
PCT Pub. Date: Dec. 10, 2015

(65) Prior Publication Data
US 2016/0361149 A1 Dec. 15, 2016

(30) Foreign Application Priority Data

Jun. 6, 2014 (JP) .................................. 2014-118156

(51) Int. Cl.
*A61C 17/00* (2006.01)
*A61C 19/06* (2006.01)
(Continued)

(52) U.S. Cl.
CPC ........ *A61C 19/066* (2013.01); *A61C 17/0211* (2013.01); *A61C 17/0217* (2013.01); *A61C 17/022* (2013.01)

(58) Field of Classification Search
CPC .............. A61C 19/066; A61C 17/0211; A61C 17/0217; A61C 17/022; A61C 17/028; A61C 3/025
(Continued)

(56) References Cited

U.S. PATENT DOCUMENTS 5,820,373 A 10/1998 Okano et al.
2008/0255498 A1* 10/2008 Houle .................... A61C 17/02
604/20

(Continued)

FOREIGN PATENT DOCUMENTS

JP H11-318949 A 11/1999
JP 2012-513455 A 6/2012
(Continued)

OTHER PUBLICATIONS

International Search Report issued in Application No. PCT/JP2015/002608 dated Jun. 23, 2015, with English translation.
(Continued)

*Primary Examiner* — Eduardo C Robert
*Assistant Examiner* — Mirayda A Aponte
(74) *Attorney, Agent, or Firm* — McDermott Will & Emery LLP

(57) ABSTRACT

A teeth whitening device includes a generator configured to generate a teeth whitening fluid that whitens teeth and humidified gas, a mouthpiece configured to supply the teeth whitening fluid and the humidified gas, and a coupling part that couples the generator and the mouthpiece with each other. The mouthpiece includes a first supply port through which the teeth whitening fluid is supplied, and a second supply port through which the humidified gas is supplied, the second supply port being separated from the first supply port. The mouthpiece further includes a first supply passage configured to guide the teeth whitening fluid to the first supply port, and a second supply passage configured to guide the humidified gas to the second supply port, the
(Continued)

second supply passage being separated from the first supply passage.

6 Claims, 21 Drawing Sheets

(51) Int. Cl.
   *A61C 17/02* (2006.01)
   *A61C 17/022* (2006.01)

(58) Field of Classification Search
   USPC .......................... 433/80, 87, 88; 604/20, 538
   See application file for complete search history.

(56) References Cited

U.S. PATENT DOCUMENTS

| | | |
|---|---|---|
| 2012/0015322 A1 | 1/2012 | Lloyd et al. |
| 2012/0040308 A1 | 2/2012 | Holbeche et al. |

FOREIGN PATENT DOCUMENTS

| | | |
|---|---|---|
| WO | 1996/010372 A1 | 4/1996 |
| WO | 2005/094719 A1 | 10/2005 |
| WO | 2010/103263 A1 | 9/2010 |
| WO | 2013/039906 A1 | 3/2013 |
| WO | 2013/155492 A1 | 10/2013 |

OTHER PUBLICATIONS

English Translation of Chinese Search Report dated Feb. 1, 2018 for the related Chinese Patent Application No. 201580011213.7.

* cited by examiner

TEETH BLEACHING APPARATUS

RELATED APPLICATIONS

This application is the U.S. National Phase under 35 U.S.C. § 371 of International Application No. PCT/JP2015/002608, filed on. May 25, 2015, which in turn claims the benefit of Japanese Application No. 2014-118156, filed on Jun. 6, 2014, the disclosures of which are incorporated by reference herein.

TECHNICAL FIELD

The present invention relates to a teeth whitening device that supplies a teeth whitening fluid to teeth.

BACKGROUND ART

Teeth whitening devices generate and supply radical species that act on pigment molecules of teeth to whiten the teeth. For example, medical teeth whitening devices for dentists are known. The medical teeth whitening devices irradiate oxygen-based bleach with ultraviolet rays or heats oxygen-based bleach to generate radical species from the oxygen-based bleach. The ultraviolet irradiation or heating is performed while supplying the oxygen-based bleach to the oral cavity. Accordingly, peroxide included in the oxygen-based bleach may touch the teeth or gums, or the teeth or gums may be irradiated with or heated by the ultraviolet rays, and this may cause damage to the teeth or gums.

Home teeth whitening devices that generate radical species without using oxygen-based bleach in view of such influence on the teeth or gums are known. PTL 1 discloses an example of such home teeth whitening devices.

A teeth whitening device according to PTL 1 includes a gas cylinder that stores gas to form plasma, and a plasma generating cell that generates plasma including radical species as active ingredients from the gas in the gas cylinder. The teeth whitening device according to PTL 1 further includes an applicator tube with a plasma outlet, and a hose that couples the plasma generating cell with the applicator tube.

A user of the teeth whitening device drives the plasma generating cell while holding the applicator tube in such a manner that the plasma outlet is directed toward a whitening target tooth. The plasma generated by the plasma generating cell is supplied to the tooth through the applicator tube.

According to PTL 1, the user is required to keep the position of his or her hand not to move the plasma outlet of the applicator tube off the whitening target tooth while using the teeth whitening device. In view of this, the teeth whitening device according to PTL 1 has room for improvement for usability.

CITATION LIST

Patent Literature

PTL 1: Japanese Translation of PCT Publication No. 2012-513455

SUMMARY OF THE INVENTION

The present invention provides a teeth whitening device that excels in usability.

According to one aspect of the present invention, there is provided a teeth whitening device includes: a generator configured to generate a teeth whitening fluid that whitens teeth and humidified gas, and a mouthpiece including a supply port through which the teeth whitening fluid and the humidified gas generated by the generator are supplied.

According to another aspect of the present invention, there is provided a teeth whitening device includes: a generator configured to generate humidified gas and generate from the humidified gas a teeth whitening fluid that whitens teeth, or a generator configured to generate a teeth whitening fluid that whitens teeth and generate a humidified gas from the fluid; and a mouthpiece including a supply port through which the teeth whitening fluid or the humidified gas generated by the generator is supplied.

DESCRIPTION OF EMBODIMENTS

First Exemplary Embodiment

Figure 1:
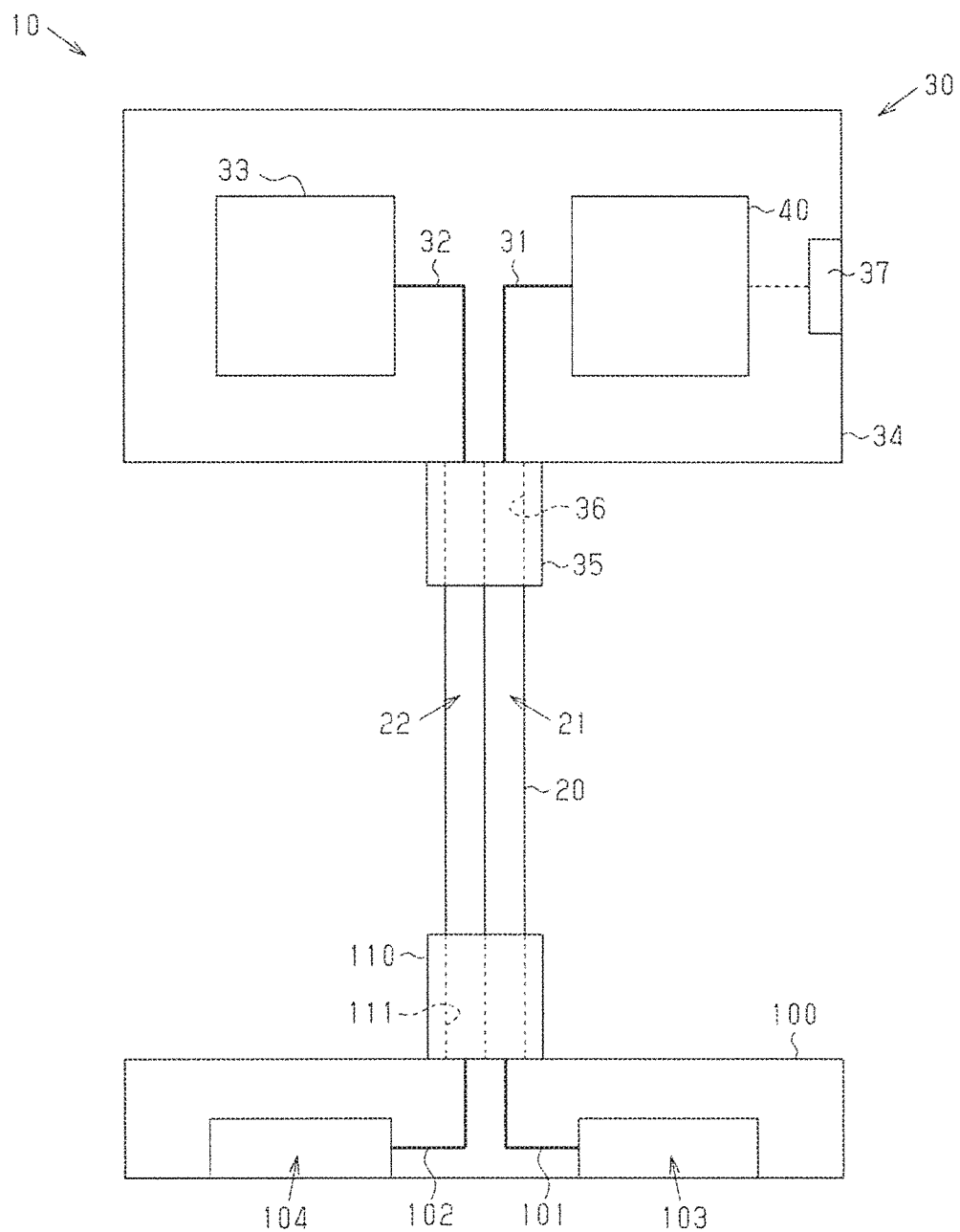
FIG. 1 is a block diagram of a teeth whitening device according to a first exemplary embodiment.

A configuration of teeth whitening device 10 according to a first exemplary embodiment is described below with reference to FIG. 1.

Teeth whitening device 10 includes generator 30 that generates teeth whitening fluid that whitens teeth and humidified gas, mouthpiece 100 that supplies the teeth whitening fluid and the humidified gas, and coupling part 20 that couples generator 30 with mouthpiece 100. One example of the teeth whitening fluid is gas containing charged microparticle water, and radical species in the charged microparticle water are an example of active ingredients for whitening teeth. One example of radical species is OH radicals.

Generator 30 includes discharger 40 that generates charged microparticle water containing radical species, humidifier 33 that generates the humidified gas, and housing 34 that accommodates various components, such as discharger 40 and humidifier 33. Generator 30 further includes a trigger that allows discharger 40 to generate the charged microparticle water, and switch 37 that forms a trigger that allows humidifier 33 to generate the humidified gas. Gas which is not humidified by humidifier 33 is supplied to discharger 40.

Housing 34 includes connector 35 that is connected with coupling part 20, first supply passage 31 that is configured to guide the teeth whitening fluid generated by discharger 40 to coupling part 20, and second supply passage 32 that is configured to guide the humidified gas generated by humidifier 33 to coupling part 20. First supply passage 31 and second supply passage 32 are separated from each other so as to prevent the fluids flowing in the passages from being mixed with each other.

Connector 35 includes connecting passage 36 that allows an inner space of housing 34 to communicate with an outside of housing 34. First supply passage 31 allows an outlet of discharger 40 to communicate with connecting passage 36. Second supply passage 32 allows an outlet of humidifier 33 to communicate with connecting passage 36.

Mouthpiece 100 includes connector 110 connected with coupling part 20, and first supply port 103 and second supply port 104 that allow an inner space of mouthpiece 100 to communicate with an outside of mouthpiece 100. First supply port 103 and second supply port 104 are separated from each other so as to prevent the fluids flowing in the passages from being mixed with each other.

Mouthpiece 100 further includes first supply passage 101 that is configured to guide the teeth whitening fluid supplied to the inner space of mouthpiece 100 to first supply port 103, and second supply passage 102 that is configured to guide the humidified gas supplied to the inner space of mouthpiece 100 to second supply port 104. First supply passage 101 and second supply passage 102 are separated from each other so as to prevent the fluids flowing in the passages from being mixed with each other.

Connector 110 includes connecting passage 111 that allows the inner space of mouthpiece 100 to communicate with the outside of mouthpiece 100. First supply passage 101 allows connecting passage 111 to communicate with first supply port 103. Second supply passage 102 allows connecting passage 111 to communicate with second supply port 104.

Coupling part 20 includes first supply passage 21 that is configured to guide the teeth whitening fluid supplied from generator 30 to mouthpiece 100, and second supply passage 22 that is configured to guide the humidified gas supplied from generator 30 to mouthpiece 100. First supply passage 21 and second supply passage 22 are separated from each other so as to prevent the fluids flowing in the passages from being mixed with each other.

One example of coupling part 20 is a single tubular object in which first supply passage 21 and second supply passage 22 are provided. Another example of coupling part 20 is two tubular objects, and first supply passage 21 is provided in one of the tubular objects and second supply passage 22 is provided in the other one of the tubular objects.

When coupling part 20 is inserted in connecting passage 36 of generator 30, the passages of generator 30 and the passages of coupling part 20 form a following connecting relationship. First supply passage 31 of generator 30 is in communication with first supply passage 21 of coupling part 20, and is not in communication with second supply passage 22 of coupling part 20. Second supply passage 32 of generator 30 is in communication with second supply passage 22 of coupling part 20, and is not in communication with first supply passage 21 of coupling part 20.

When coupling part 20 is inserted in connecting passage 111 of mouthpiece 100, the passages of mouthpiece 100 and the passages of coupling part 20 form a following connecting relationship. First supply passage 101 of mouthpiece 100 is in communication with first supply passage 21 of coupling part 20, and is not in communication with second supply passage 22 of coupling part 20. Second supply passage 102 of mouthpiece 100 is in communication with second supply passage 22 of coupling part 20, and is not in communication with first supply passage 21 of coupling part 20.

Operation of teeth whitening device 10 is described below.

A user places mouthpiece 100 in his or her oral cavity, and holds mouthpiece 100 by closing the mouth. Then, by turning on switch 37, discharger 40 and humidifier 33 are activated to generate a teeth whitening fluid containing charged microparticle water and a humidified gas, respectively.

The teeth whitening fluid generated by discharger 40 flows into first supply passage 31 of generator 30, first supply passage 21 of coupling part 20, and first supply passage 101 of mouthpiece 100 in this order. The teeth whitening fluid of first supply passage 101 is supplied to the oral cavity of the user from first supply port 103. Thus, the charged microparticle water reaches the teeth of the user, and radical species contained in the charged microparticle water removes electrons from colored organic substances on the teeth. As a result, the colored organic substances are decomposed and the teeth are whitened.

The humidified gas generated by humidifier 33 flows into second supply passage 32 of generator 30, second supply passage 22 of coupling part 20, and second supply passage 102 of mouthpiece 100 in this order. The humidified gas of second supply passage 102 is supplied to the oral cavity of the user from second supply port 104. Thus, the humidified gas reaches organs in the oral cavity, such as gums and a tongue, to suppress drying of the organs.

Teeth whitening device 10 according to the first exemplary embodiment has the following advantageous effects.

(1) Teeth whitening device 10 includes generator 30 and mouthpiece 100. With this configuration, the user places mouthpiece 100 that is an object to supply the teeth whitening fluid into his or her oral cavity, thereby enabling the user to hold the object at a position suitable for whitening his or her teeth. In other words, the user can whiten his or her teeth without holding the object that supplies the teeth whitening fluid with his or her hand. Thus, teeth whitening device 10 can provide usability for the user.

(2) According to the configuration as described in the above (1), the user hardly feels fatigue on his or her hand when using teeth whitening device 10. Teeth whitening device 10 can provide usability also in this regard.

(3) According to the configuration as described in the above (1), the user can freely use his or her hands even when using teeth whitening device 10. Thus, the user can do other things while whitening the teeth. Teeth whitening device 10 can provide usability also in this regard.

(4) According to the configuration as described in the above (1), first supply port 103 is hardly displaced with respect to the teeth while the user is using teeth whitening device 10 as compared to a case in which the user holds the object that supplies the teeth whitening fluid to the teeth with his or her hand. Thus, the teeth whitening fluid supplied from first supply port 103 to the oral cavity is efficiently supplied to the teeth.

(5) Generator 30 includes humidifier 33. With this configuration, the humidified gas is supplied from mouthpiece 100 to the oral cavity, and thus the oral cavity is not easily dried even if the user does not particularly supply water to his or her oral cavity. Teeth whitening device 10 can provide usability also in this regard.

(6) Mouthpiece 100 includes first supply port 103 and second supply port 104 that are separated from each other. With this configuration, the teeth whitening fluid and the humidified gas are not easily mixed with each other before being supplied to the oral cavity. This reduces the possibility of deactivation that is caused when active ingredients contained in the teeth whitening fluid is mixed with the humidified gas. As a result, the teeth can be whitened efficiently as compared to a case in which mouthpiece 100 does not include first supply port 103 and second supply port 104 that are separated from each other.

(7) Mouthpiece 100 includes first supply passage 101 and second supply passage 102 that are separated from each other. With this configuration, the teeth whitening fluid and the humidified gas are hardly mixed with each other when passing through mouthpiece 100. Thus, possibility of deactivation that is caused when active ingredients contained in the teeth whitening fluid is mixed with the humidified gas is further reduced. As a result, the teeth can be whitened efficiently as compared to a case in which mouthpiece 100 does not include first supply passage 101 and second supply passage 102 that are separated from each other.

(8) The radical species contained in the teeth whitening fluid may be deactivated due to various reasons before acting on the teeth. For example, in the case in which the teeth whitening fluid and the humidified gas are mixed with each other before being supplied to the oral cavity, the radical species may be replaced with other substance by collision with water particles contained in the humidified gas. In the case in which the teeth whitening fluid passes through a passage where the humidified gas has passed, the radical species may be adsorbed by water adhered from the humidified gas to wall surfaces of various objects. Meanwhile, each of the configurations in the above (6) and (7) contributes to reducing the possibility of deactivation of the radical species as described above. Thus, the teeth whitening fluid is efficiently supplied to the teeth as compared to a case where mouthpiece 100 does not include the configuration described in (6) or (7).

(9) Teeth whitening device 10 includes coupling part 20. With this configuration, the user can place mouthpiece 100 in his or her oral cavity even if the user is away from generator 30, and thus the user can whiten his or her teeth in a relatively free posture. Teeth whitening device 10 can provide usability also in this regard.

(10) In the case where the teeth whitening fluid is to be generated by allowing the humidified gas to create corona discharge, corona discharge may be prevented due to dew condensation on electrodes. Meanwhile, teeth whitening device 10 supplies non-humidified gas to discharger 40. Thus, the teeth whitening fluid is efficiently generated by discharger 40.

Second Exemplary Embodiment

A configuration of teeth whitening device 10 according to a second exemplary embodiment is described below with reference to FIGS. 2 to 4. Teeth whitening device 10 according to the second exemplary embodiment includes the following configuration that is not explicitly described in the description regarding the teeth whitening device 10 according to the first exemplary embodiment.

Figure 2:
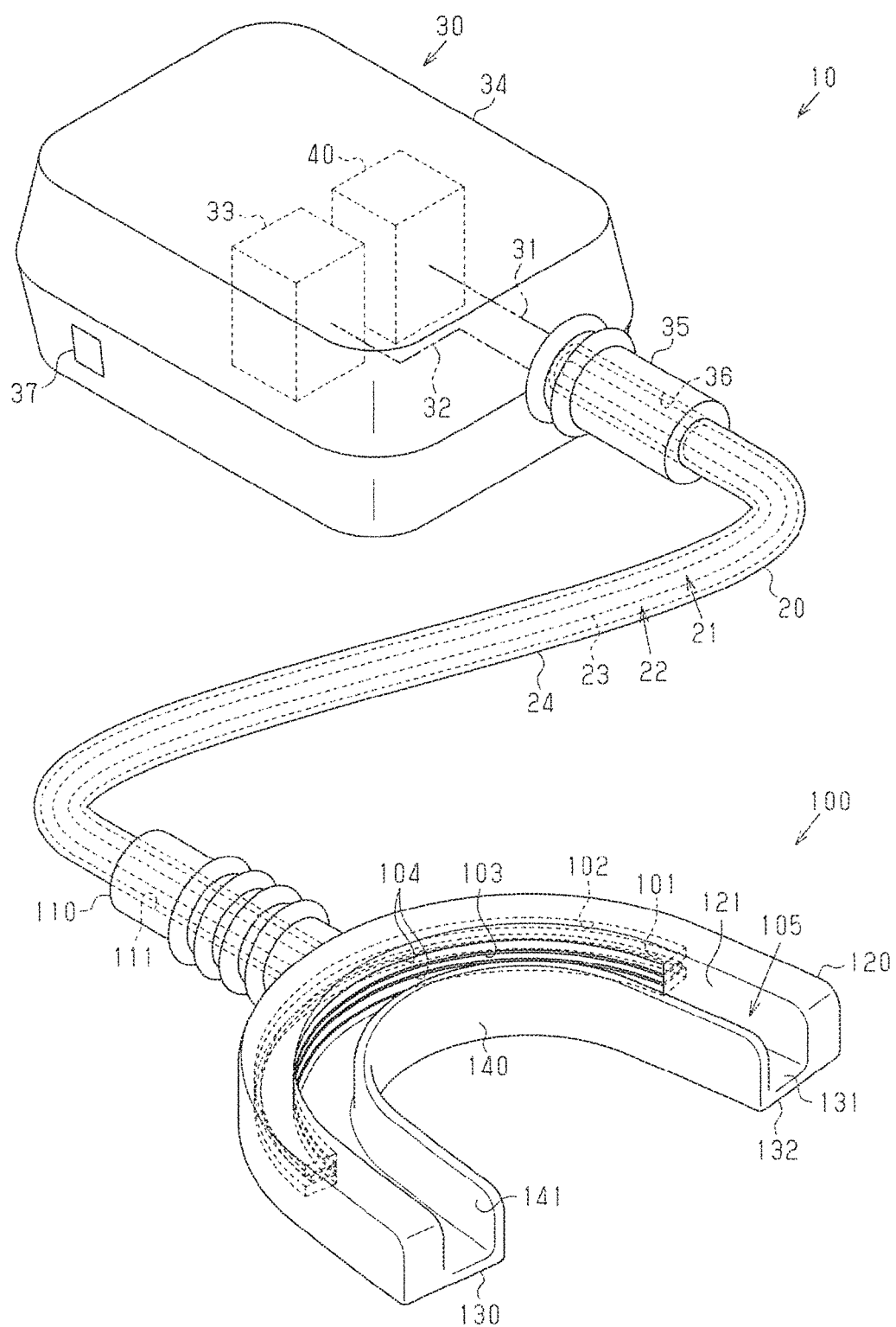
FIG. 2 is a perspective view of a teeth whitening device according to a second exemplary embodiment.

FIG. 2 shows a structure of teeth whitening device 10 in a perspective view.

Generator 30 and coupling part 20 include a connecting structure that allows a user to arbitrarily select a state between a state in which coupling part 20 is connected to generator 30 and a state in which coupling part 20 is separated from generator 30. Mouthpiece 100 and coupling part 20 include a connecting structure that allows the user to arbitrarily select a state between a state in which coupling part 20 is connected to mouthpiece 100 and a state in which coupling part 20 is separated from mouthpiece 100.

One example of coupling part 20 is a hose that couples connector 35 of housing 34 with connector 110 of mouthpiece 100. A material of the hose is, for example, a resin having a high flexibility. The hose has a double tube structure including an inner tube 23 and an outer tube 24. Inner tube 23 includes first supply passage 21 formed therein. Second supply passage 22 is provided between inner tube 23 and outer tube 24.

Figure 3:
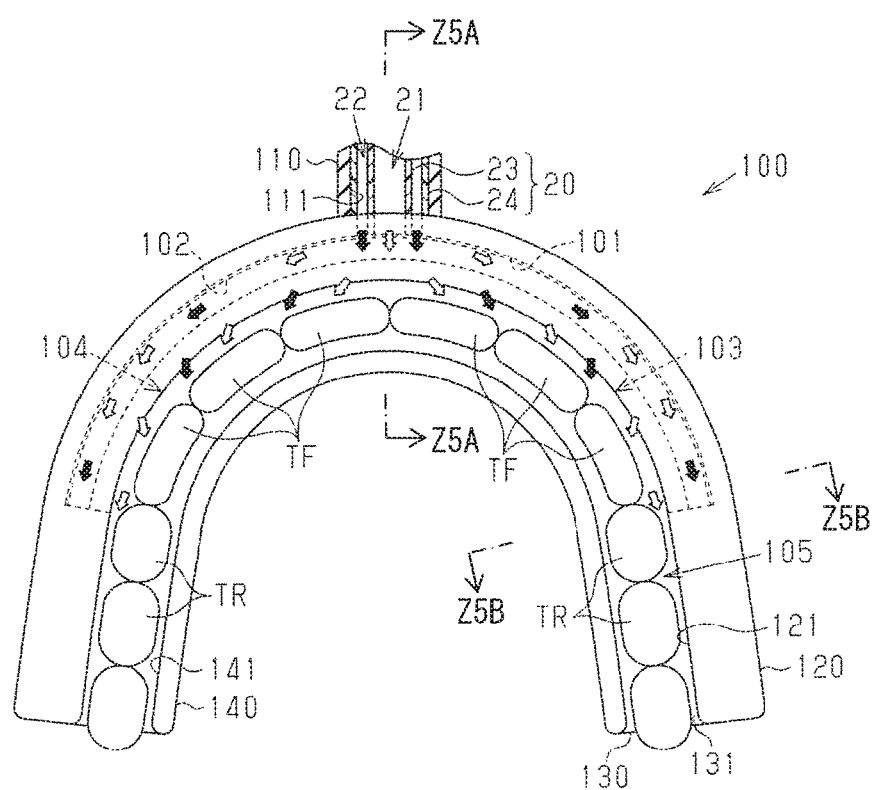
FIG. 3 is a plan view of a mouthpiece according to the second exemplary embodiment.

FIG. 3 shows a structure of mouthpiece 100 in a plan view.

Mouthpiece 100 has, for example, a symmetrical shape with respect to a center line in a lateral direction in a plan view, and can have various sizes according to the user's age or the like. One example of a material of mouthpiece 100 is a silicone rubber.

Mouthpiece 100 further includes, in addition to connector 110, outer curved element 120 curved to guide a teeth whitening fluid, occluded element 130 projecting from outer curved element 120, and inner curved element 140 projecting from occluded element 130. Occluded element 130 and inner curved element 140 are curved in accordance with the shape of outer curved element 120. Mouthpiece 100 further includes teeth receiving space 105 surrounded by outer curved element 120, occluded element 130, and inner curved element 140.

Outer curved element 120 includes first supply passage 101, second supply passage 102, first supply port 103, and second supply port 104, and further includes guiding surface 121 configured to guide the teeth whitening fluid. First supply passage 101 and second supply passage 102 are formed in outer curved element 120, and are separated from each other by a part of outer curved element 120. First supply port 103 and second supply port 104 are opened in guiding surface 121, and are separated from each other by a part of outer curved element 120.

First supply passage 101 and the like have the following forms, for example. First supply passage 101 and first supply port 103, and second supply passage 102 and second supply port 104 are formed in an extending direction of outer curved element 120. First supply passage 101 and second supply passage 102 are formed side by side in a height direction of outer curved element 120. Second supply passage 102 is formed to sandwich first supply passage 101 in a height direction of outer curved element 120.

In the illustrated example, a part of first supply passage 101 curved in accordance with the shape of outer curved element 120 and a part of second supply passage 102 curved in accordance with the shape of outer curved element 120 are substantially overlapped with each other in a plan view of outer curved element 120. With reference to FIGS. 3 and 4, a part of surfaces forming second supply passage 102 is illustrated as shifted from first supply passage 101 to indicate presence of first supply passage 101 and second supply passage 102.

Occluded element 130 projects inward from outer curved element 120 and includes inner surface 131 and outer surface 132 that relatively have a front/back relationship. Inner curved element 140 is an element projecting from inner surface 131 of occluded element 130 in a height direction of mouthpiece 100, and includes guiding surface 141 that faces guiding surface 121 of outer curved element 120.

An operation of teeth whitening device 10 is described with reference to FIG. 4.

The user places mouthpiece 100 into his or her oral cavity in such a manner that upper teeth or lower teeth are placed in teeth receiving space 105 of mouthpiece 100 and bites occluded element 130 with his or her upper teeth and lower teeth to hold mouthpiece 100. When mouthpiece 100 is placed in the oral cavity, guiding surface 121 of outer curved element 120 is opposed to a front surface of the teeth across a part of teeth receiving space 105, and guiding surface 141 of inner curved element 140 is opposed to a back surface of the teeth across a part of teeth receiving space 105. Further, inner surface 131 of occluded element 130 contacts the upper teeth and outer surface 132 of occluded element 130 contacts the lower teeth.

Figure 4:
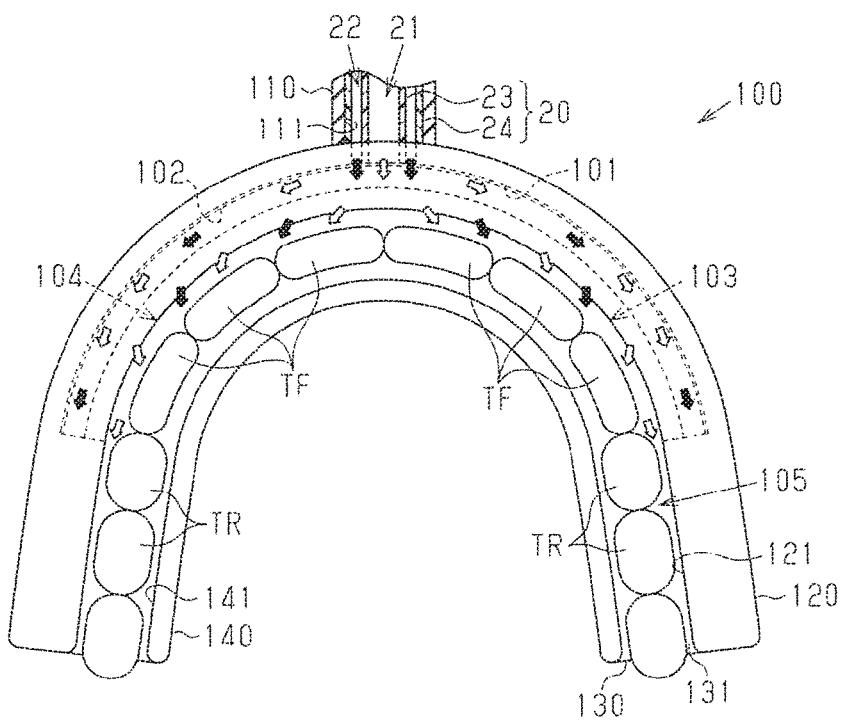
FIG. 4 is a plan view of the mouthpiece according to the second exemplary embodiment.

White arrows shown in FIG. 4 roughly indicate a flow of the teeth whitening fluid supplied to the oral cavity passing through coupling part 20 and mouthpiece 100 and a flow of the teeth whitening fluid inside the oral cavity. Black arrows shown in FIG. 4 roughly indicate a flow of the humidified gas supplied to the oral cavity passing through coupling part 20 and mouthpiece 100 and a flow of the humidified gas inside the oral cavity. Note that white arrows and black arrows shown in FIGS. 5A, 5B, 10, 11, 13, 16, 19A, and 19B indicate flows of the teeth whitening fluid and the humidified gas same as or similar to flows of the teeth whitening fluid and the humidified gas indicated by the arrows shown in FIG. 4.

The teeth whitening fluid generated by generator 30 flows into first supply passage 31 of generator 30, first supply passage 21 of coupling part 20, and first supply passage 101 of mouthpiece 100 in this order. The teeth whitening fluid of first supply passage 101 is supplied from first supply port 103 to teeth receiving space 105. Thus, the teeth whitening fluid supplied to teeth receiving space 105 reaches front teeth TF or rear teeth TR to whiten the teeth. The teeth whitening fluid of teeth receiving space 105 is guided by guiding surface 121 of outer curved element 120 and flows in teeth receiving space 105 along the teeth. Accordingly, the teeth whitening fluid reaches substantially all of the upper and lower teeth and whitens the teeth.

The humidified gas generated by generator 30 flows into second supply passage 32 of generator 30, second supply passage 22 of coupling part 20, and second supply passage 102 of mouthpiece 100 in this order. The humidified gas of second supply passage 102 is supplied from second supply port 104 to teeth receiving space 105. Thus, the humidified gas supplied to teeth receiving space 105 reaches organs, such as the gums and tongue, to suppress drying of the organs.

Teeth whitening device 10 according to second exemplary embodiment has the following advantageous effects in addition to (1) to (10) achieved by teeth whitening device 10 according to the first exemplary embodiment.

(11) Teeth whitening device 10 includes coupling part 20 having a double tube structure. With this configuration, the user easily pulls around mouthpiece 100 when placing mouthpiece 100 into his or her oral cavity as compared to a case in which a plurality of coupling parts are separately formed. The teeth whitening device can provide usability also in this regard.

(12) Mouthpiece 100 includes outer curved element 120. With this configuration, the teeth whitening fluid supplied to teeth receiving space 105 is guided by guiding surface 121 of outer curved element 120 and thus easily flows along the teeth. Thus, the teeth are efficiently whitened as compared to a case in which mouthpiece 100 does not include outer curved element 120.

(13) First supply port 103 is opened in guiding surface 121 of outer curved element 120. With this configuration, the teeth whitening fluid supplied from first supply port 103 to the oral cavity easily reaches the teeth. Thus, the teeth are efficiently whitened as compared to a case in which first supply port 103 is not opened in guiding surface 121.

(14) Second supply port 104 is opened in guiding surface 121 of outer curved element 120. With his configuration, the humidified gas supplied from second supply port 104 to the oral cavity easily reaches the gums. Thus, drying of the gums are efficiently suppressed as compared to a case in which second supply port 104 is not opened in guiding surface 121.

Third Exemplary Embodiment

Figure 5A:
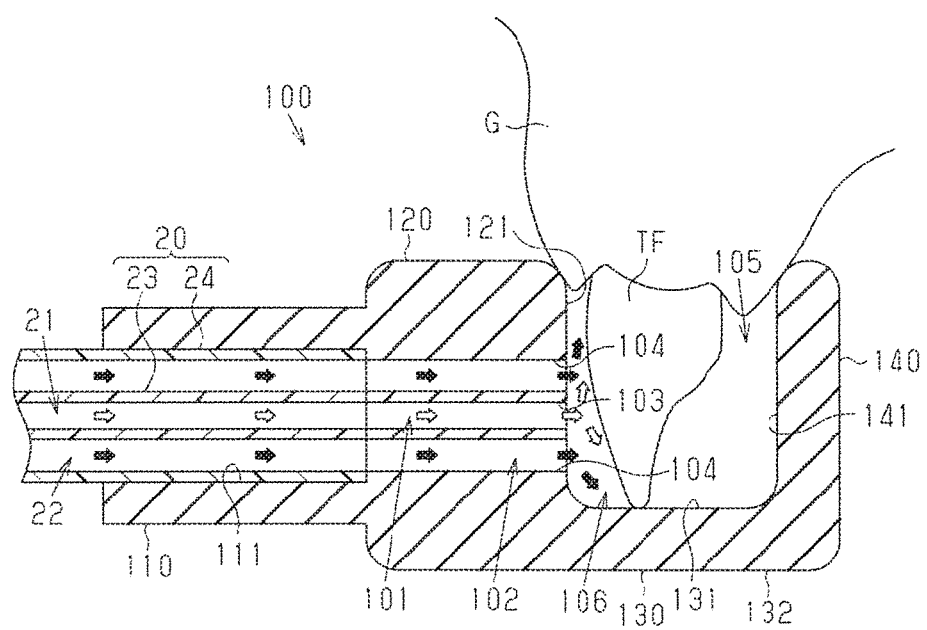
FIG. 5A is a sectional view taken along line Z5A-Z5A in FIG. 3 according to a third exemplary embodiment.
Figure 5B:
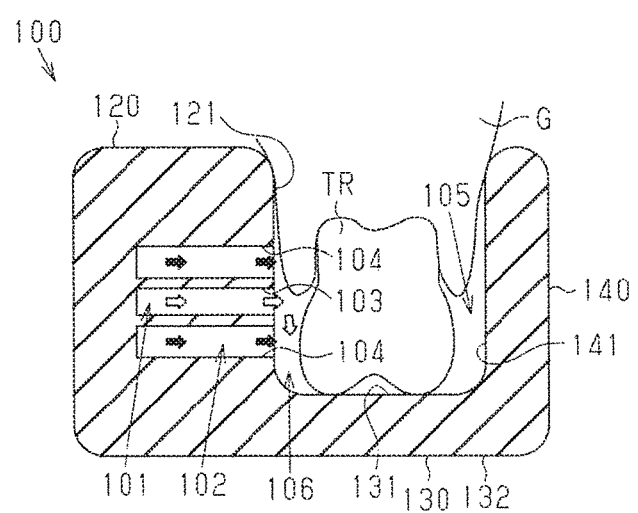
FIG. 5B is a sectional view taken along line Z5B-Z5B in FIG. 3 according to the third exemplary embodiment.

With reference to FIGS. 5A and 5B, a configuration of teeth whitening device 10 according to a third exemplary embodiment is described below. Teeth whitening device 10 according to the third exemplary embodiment includes a following configuration that is not explicitly described in the description regarding teeth whitening device 10 according to the second exemplary embodiment.

FIG. 5A shows front teeth TF and surroundings of front teeth TF in a user's oral cavity in which mouthpiece 100 is placed. FIG. 5B shows rear teeth TR and surroundings of rear teeth TR in the oral cavity of the user in which mouthpiece 100 is placed.

In one example, a height of teeth receiving space 105 is set in such a manner that roots of front teeth TF and rear teeth TR that are in contact with gums G are accommodated in teeth receiving space 105. Note that the height of teeth receiving space 105 is equal to a distance between inner surface 131 of occluded element 130 and a top surface of outer curved element 120 or a top surface of inner curved element 140.

In one example, a width of teeth receiving space 105 is set to form guiding passage 106 that is a gap having an appropriate size between guiding surface 121 of outer curved element 120 and front teeth TF and rear teeth TR. Note that the width of teeth receiving space 105 is equal to a distance between guiding surface 121 of outer curved element 120 and guiding surface 141 of inner curved element 140 in a direction in which occluded element 130 projects from guiding surface 121.

In one example, a width of an opening of teeth receiving space 105 is set in such a manner that guiding surface 121 of outer curved element 120 and guiding surface 141 of inner curved element 140 come in contact at a suitable pressure with the roots of front teeth TF and rear teeth TR that are in contact with gums G. In the illustrated example, the width of the opening of teeth receiving space 105 is set to be the same as the width of teeth receiving space 105.

As illustrated in FIG. 5A, when mouthpiece 100 is placed in the oral cavity, the incisal edges of upper front teeth TF comes in contact with inner surface 131 of occluded element 130, and the incisal edges of the lower front teeth (not shown) comes in contact with outer surface 132 of occluded element 130. Guiding surface 121 of outer curved element 120 forms guiding passage 106 with front teeth TF. Guiding surface 121 of outer curved element 120 makes firm contact with a front surface of upper gums G at the roots of front teeth TF. Guiding surface 141 of inner curved element 140 makes firm contact with a back surface of upper gums G at the roots of front teeth TF.

As illustrated in FIG. 5B, when mouthpiece 100 is placed in the oral cavity, an occlusal surface of upper rear teeth TR comes in contact with inner surface 131 of occluded element 130, and an occlusal surface of the lower rear teeth (not shown) comes in contact with outer surface 132 of occluded element 130. Guiding surface 121 of outer curved element 120 forms guiding passage 106 with rear teeth TR. Guiding surface 121 of outer curved element 120 makes firm contact with a front surface of the upper gums G at the roots of rear teeth TR. Guiding surface 141 of inner curved element 140 makes firm contact with a back surface of upper gums G at the roots of rear teeth TR.

An operation of teeth whitening device 10 is described below with reference to FIGS. 5A and 5B.

As illustrated in 5A, the teeth whitening fluid is supplied from first supply passage 21 of coupling part 20 to first supply passage 101 of mouthpiece 100. The teeth whitening fluid of first supply passage 101 is supplied to guiding passage 106 from an intermediate part of first supply port 103. Thus, the teeth whitening fluid reaches front teeth TF, and whitens the teeth.

The humidified gas is supplied from second supply passage 22 of coupling part 20 to second supply passage 102 of mouthpiece 100. The humidified gas of second supply passage 102 is supplied from an intermediate part of second supply port 104 to guiding passage 106. Thus, the humidified gas reaches gums G at the roots of front teeth TF, and suppresses drying of the organs.

As illustrated in FIG. 5B, the teeth whitening fluid of first supply passage 101 is supplied to guiding passage 106 from a part of first supply port 103 nearer to the end than the intermediate part. Thus, the teeth whitening fluid reaches rear teeth TR and whitens the teeth.

The humidified gas of second supply passage 102 is supplied to guiding passage 106 from a part of second supply port 104 nearer to the end than the intermediate part. Thus, the humidified gas reaches gums G at the roots of rear teeth TR, and suppresses drying of the organ.

The teeth whitening fluid in guiding passage 106 is guided by guiding surface 121 of outer curved element 120 to flow through guiding passage 106 along the teeth. Thus, the teeth whitening fluid reaches substantially all of the upper teeth and the lower teeth, and whitens the teeth.

The humidified gas of guiding passage 106 is guided by guiding surface 121 of outer curved element 120 to flow through guiding passage 106 along the teeth. Thus, the humidified gas reaches substantially all of upper gums G and lower gums G, and suppresses drying of such organs.

Teeth whitening device 10 according to the third exemplary embodiment has the following advantageous effects in addition to (1) to (14) achieved by teeth whitening device 10 according to the second exemplary embodiment.

(15) A width of teeth receiving space 105 is set so as to form guiding passage 106 between outer curved element 120 and front teeth TF and rear teeth TR. With this configuration, the teeth whitening fluid supplied from first supply port 103 to guiding passage 106 easily flows along the teeth. Thus, differences of the degree of whitening among the teeth are minimally increased.

(16) According to the configuration as described in the above (15), first supply port 103 is hardly blocked by the teeth. Thus, a flow of the teeth whitening fluid from first supply port 103 toward guiding passage 106 is hardly obstructed. Accordingly, the teeth whitening fluid is efficiently supplied to the teeth as compared to a case in which teeth whitening device 10 does not include the configuration described in the above (15).

(17) According to the configuration as described in the above (15), second supply port 104 is hardly blocked by the teeth. Thus, a flow of the humidified gas from second supply port 104 toward guiding passage 106 is hardly obstructed. Accordingly, the humidified gas is efficiently supplied to the organs, such as the gums, as compared to a case in which teeth whitening device 10 does not include the configuration described in the above (15).

Fourth Exemplary Embodiment

Figure 6:
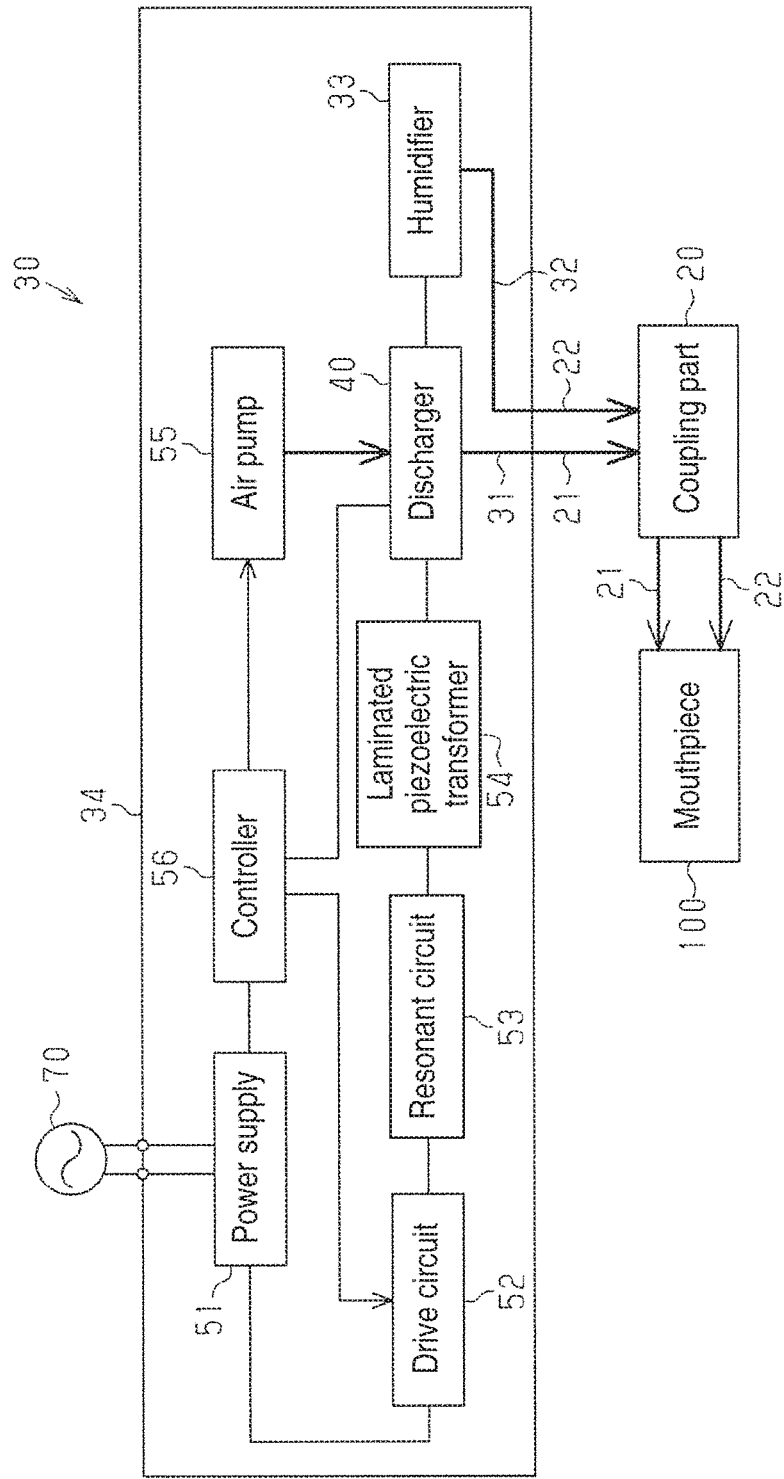
FIG. 6 is a block diagram of a teeth whitening device according to a fourth exemplary embodiment.

A configuration of teeth whitening device 10 according to a fourth exemplary embodiment is described below with reference to FIG. 6. Teeth whitening device 10 according to the fourth exemplary embodiment includes the following configuration that is not explicitly described in the description regarding teeth whitening device 10 according to the third exemplary embodiment.

Generator 30 further includes, in addition to housing 34, humidifier 33, and discharger 40, power supply 51 that rectifies power supplied from commercial power supply 70, and drive circuit 52 that changes a frequency of power from power supply 51 and outputs the changed frequency. Generator 30 further includes resonant circuit 53 that increases a voltage supplied from drive circuit 52, and laminated piezoelectric transformer 54 that converts a voltage supplied from resonant circuit 53 to high voltage and outputs the high voltage. Generator 30 further includes air pump 55 that supplies air to discharger 40, and controller 56 that controls humidifier 33, drive circuit 52, discharger 40, and air pump 55. Housing 34 houses humidifier 33, discharger 40, power supply 51, drive circuit 52, resonant circuit 53, laminated piezoelectric transformer 54, air pump 55, and controller 56.

Power supply 51 includes, for example, a diode bridge, and includes a rectifier circuit that performs full-wave rectification of AC power supplied from commercial power supply 70 and a capacitor that eliminates noise from the power rectified by the rectifier circuit.

Drive circuit 52 is electrically connected with power supply 51, and includes a single-phase full bridge inverter, for example. The inverter includes two arms connected in parallel, and each of the arms includes two metal-oxide-semiconductor field-effect transistors (MOSFETs) connected in series. Drive circuit 52 generates AC power having a higher frequency than AC power supplied from commercial power supply 70 by switching on and off of the four MOSFETs.

Resonant circuit 53 is, for example, a series LC resonant circuit, and includes a circuit configuration in which drive circuit 52, a reactor, and a primary electrode of laminated piezoelectric transformer 54 are connected in series. Resonant circuit 53 increases power supplied from drive circuit 52 and supplies the increased power to laminated piezoelectric transformer 54.

Figure 7:
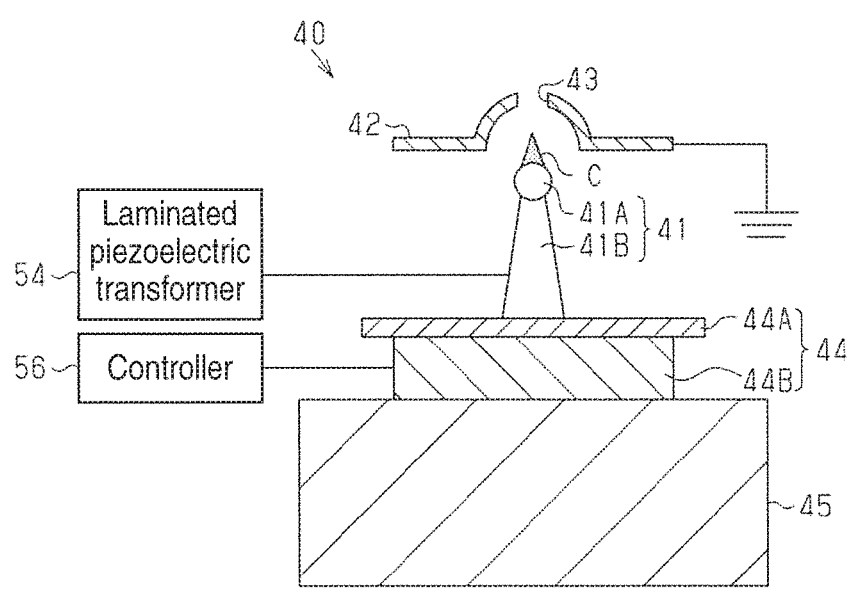
FIG. 7 is a sectional view of a discharger according to a fifth exemplary embodiment.

Laminated piezoelectric transformer 54 includes the above primary electrode that is electrically connected with resonant circuit 53 and a secondary electrode that is electrically connected with an electrode of discharger 40. Laminated piezoelectric transformer 54 transforms AC power supplied from resonant circuit 53 and outputs the transformed AC power to the electrode of discharger 40. Note that one example of the electrode of discharger 40 is atomization electrode 41 shown in FIG. 7.

Discharger 40 generates discharge by utilizing power supplied from laminated piezoelectric transformer 54 to generate charged microparticle water. Discharge generated by discharger 40 is corona discharge, for example. Radical species contained in the charged microparticle water generated by discharge include OH radicals.

Air pump 55 is disposed at a position where air can be supplied toward the electrode of discharger 40 and its surroundings. Air flows to pass by the electrode of discharger 40 and its surroundings by driving air pump 55. The air supplied to the electrode of discharger 40 and its surroundings flows into first supply passage 21 of coupling part 20 together with the charged microparticle water generated by discharger 40 through first supply passage 31 of generator 30.

Controller 56 controls operation of drive circuit 52 by outputting a control signal to each of the MOSFETs of drive circuit 52. Controller 56 further controls operation of air pump 55 by outputting a control signal to air pump 55, and controls operation of humidifier 33 by outputting a control signal to humidifier 33. Controller 56 starts the operation of drive circuit 52, air pump 55, and humidifier 33 when switch 37 of generator 30 is turned on, for example.

Teeth whitening device 10 according to fourth exemplary embodiment has the following advantageous effects in addition to (1) to (17) achieved by teeth whitening device 10 according to the third exemplary embodiment.

(18) Teeth whitening device 10 includes air pump 55. With this configuration, the discharge pressure of air pump 55 allows the teeth whitening fluid to be supplied from generator 30 to mouthpiece 100. Thus, the teeth whitening fluid appropriately flows from generator 30 into the oral cavity. Accordingly, the teeth are efficiently whitened as compared to a case in which teeth whitening device 10 does not include air pump 55.

Fifth Exemplary Embodiment

A configuration of teeth whitening device 10 according to a fifth exemplary embodiment is described below with reference to FIG. 7. Teeth whitening device 10 according to fifth exemplary embodiment includes the following configuration that is not explicitly described in the description regarding teeth whitening device 10 according to the fourth exemplary embodiment.

FIG. 7 shows one example of a model of discharger 40. Discharger 40 includes atomization electrode 41 configured to generate charged microparticle water, a counter electrode 42 spaced away from atomization electrode 41, cooling module 44 configured to cool atomization electrode 41, and cooling fin 45 configured to cool cooling module 44.

One example of a material forming atomization electrode 41 is a conductive metal. Barrel 41B of atomization electrode 41 is provided on cooling insulating plate 44A constituting cooling module 44. A tip end of barrel 41B includes spherical head 41A, for example. The shape of barrel 41B is, for example, a truncated cone tapered from a side of cooling module 44 to head 41A.

One example of a material forming counter electrode 42 is a conductive metal. Counter electrode 42 is grounded. Counter electrode 42 includes a curved part having a substantially semi-spherical shape. The curved part includes discharge port 43 that is in communication with a gap between atomization electrode 41 and counter electrode 42 and a space outside of counter electrode 42.

Cooling module 44 includes cooling insulating plate 44A configured to absorb heat from atomization electrode 41, and Peltier module 44B configured to cool cooling insulating plate 44A and atomization electrode 41. One example of a material forming cooling insulating plate 44A is a material having a high thermal conductivity and high electrical resistance, such as alumina. Cooling insulating plate 44A is disposed between atomization electrode 41 and Peltier module 44B.

One example of a material forming cooling fin 45 is a material having a high thermal conductivity, such as alumina. Cooling fin 45 is attached to Peltier module 44B in such a manner that Peltier module 44B is held between cooling fin 45 and cooling insulating plate 44A. Thus, heat of Peltier module 44B is radiated through cooling fin 45.

Controller 56 is electrically connected with Peltier module 44B that is a part of discharger 40, and is configured to control operation of Peltier module 44B. Peltier module 44B is operated to cool atomization electrode 41. Thus, water is adhered to a surface of head 41A and a surface of barrel 41B of atomization electrode 41, and condensed on atomization electrode 41. In a state in which water is condensed on atomization electrode 41, electric power is supplied from laminated piezoelectric transformer 54 to atomization electrode 41. The water on the surface of head 41A and the surface of barrel 41B of atomization electrode 41 is collected to the surface of head 41A by Coulomb force and Taylor cone C is formed on head 41A.

When discharge is generated between atomization electrode 41 and counter electrode 42 in a state in which Taylor cone C is formed on head 41A, charged microparticle water containing radical species is generated from Taylor cone C. This charged microparticle water flows into first supply passage 31 (see FIG. 2) of generator 30 together with air supplied from air pump 55 (see FIG. 6) through discharge port 43 of counter electrode 42.

Teeth whitening device 10 according to fifth exemplary embodiment has the following effects in addition to (1) to (18) achieved by teeth whitening device 10 according to fourth exemplary embodiment.

(19) Discharger 40 is configured to supply water to atomization electrode 41 by allowing cooling module 44 to cool atomization electrode 41. With this configuration, the size of generator 30 is easily reduced as compared to a case in which water is supplied from a water absorbing tank to atomization electrode 41, for example.

Sixth Exemplary Embodiment

A configuration of teeth whitening device 10 according to a sixth exemplary embodiment is described below with reference to FIGS. 8 to 11. Teeth whitening device 10 according to the sixth exemplary embodiment includes mouthpiece 200 shown in FIG. 8, instead of mouthpiece 100 of teeth whitening device 10 according to the first exemplary embodiment shown in FIG. 1.

Mouthpiece 200 has, for example, a symmetrical shape with respect to the center line in the lateral direction in a plan view and can have various sizes according to the user's age or the like. One example of a material forming mouthpiece 200 is a silicone rubber.

Mouthpiece 200 includes first supply port 203 and second supply port 204 that allow an inner space of mouthpiece 200 to communicate with an outside of mouthpiece 200, and connector 210 connected with coupling part 20. Mouthpiece 200 further includes first supply passage 201 configured to guide teeth whitening fluid supplied to the inner space of mouthpiece 200 to first supply port 203, and second supply passage 202 configured to guide humidified gas supplied to the inner space of mouthpiece 200 to second supply port 204. First supply passage 201 and second supply passage 202 are separated from each other so as to prevent the fluids flowing in the passages from being mixed with each other.

Mouthpiece 200 further includes curved element 220 that is curved so as to guide the teeth whitening fluid, hollow barrel 230 that connects connector 210 and curved element 220, and partition element 270 disposed inside barrel 230. Mouthpiece 200 further includes two flanges 240 projecting from curved element 220, two rims 250 projecting from a periphery of barrel 230, and two ribs 260 formed between curved element 220 and rims 250. Each of the flanges 240 is curved in accordance with a shape of curved element 220.

Mouthpiece 200 further includes upper lip receiving space 205 surrounded by a back surface of curved element 220, a top surface of barrel 230, and a side surface of one of rims 250, and lower lip receiving space 205 surrounded by the back surface of curved element 220, a bottom surface of barrel 230, and a side surface of one of rims 250.

In one example, connector 210, curved element 220, barrel 230, two flanges 240, two rims 250, and two ribs 260 are integrally molded resin element, and partition element 270 is another resin element.

Figure 9:
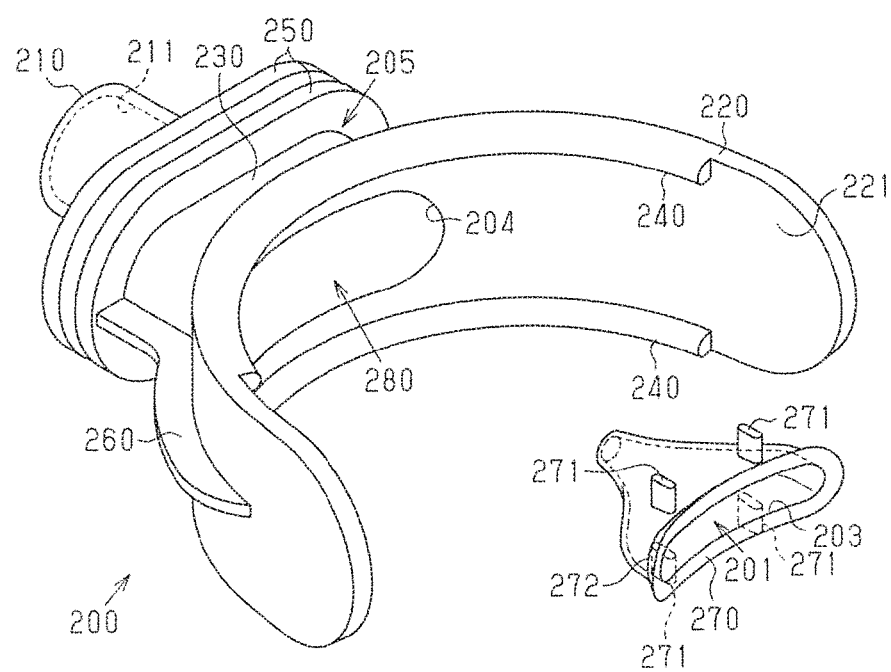
FIG. 9 is an exploded perspective view of the mouthpiece according to the sixth exemplary embodiment.

FIG. 9 shows a structure of mouthpiece 200 in an exploded perspective view.

One example of barrel 230 is an oval tube. Element accommodating space 280 in which partition element 270 is inserted is formed inside barrel 230 and curved element 220. A part of element accommodating space 280 on a side of guiding surface 221 is gradually inclined outward in a direction orthogonal to a center axis of barrel 230 from a side of connector 210 to a side of guiding surface 221.

Partition element 270 includes a plurality of supporting projections 271 configured to hold a shape of partition element 270 in such a manner that second supply passage 202 is formed between an inner surface of barrel 230 and an inner surface of curved element 220, first supply passage 201, and first supply port 203. Partition element 270 further includes inclined part 272 that directs second supply port 204 to a direction different from first supply port 203.

Inclined part 272 is formed on an outer periphery of an opening of partition element 270 on a side of first supply port 203, and is gradually inclined outward in a direction orthogonal to a center axis of partition element 270 from a side of connector 210 to a side of first supply port 203.

Partition element 270 is inserted in element accommodating space 280 and supporting projections 271 are firmly attached to an inner surface of barrel 230. As a result, partition element 270 is fixed to barrel 230 to form mouthpiece 200 shown in FIG. 8.

Figure 8:
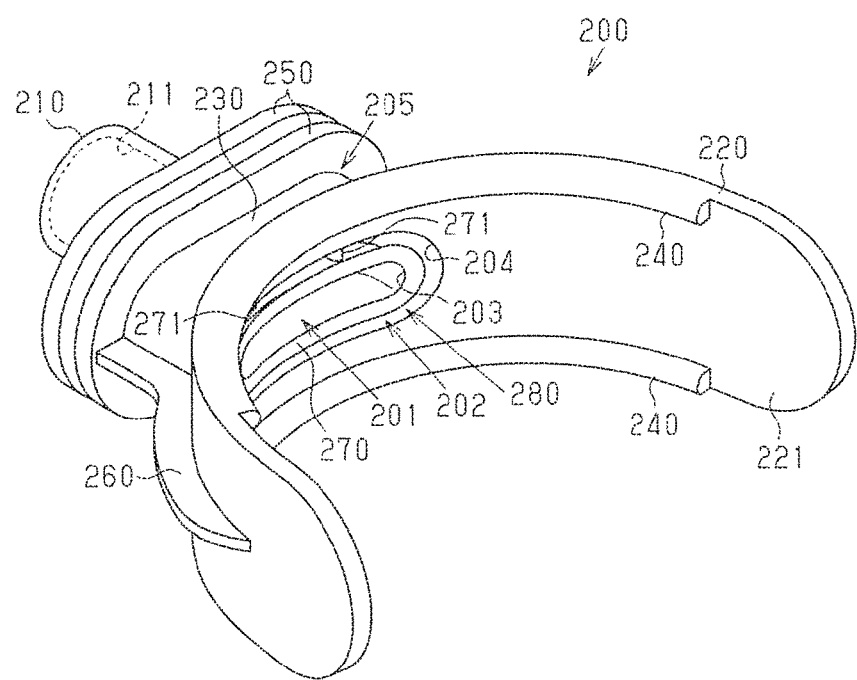
FIG. 8 is a perspective view of a mouthpiece according to a sixth exemplary embodiment.

As illustrated in FIG. 8, in mouthpiece 200, element accommodating space 280 is partitioned by partition element 270, and second supply passage 202 and second supply port 204 are formed by a part of element accommodating space 280 surrounded by an inner surface of barrel 230, an inner surface of curved element 220, and an outer surface of partition element 270.

Connector 210 includes connecting passage 211 that allows element accommodating space 280 of mouthpiece 200 to communicate with the outside of mouthpiece 200. First supply passage 201 allows connecting passage 211 to communicate with first supply port 203. Second supply passage 202 allows connecting passage 211 to communicate with second supply port 204.

Curved element 220 includes guiding surface 221 that is configured to guide the teeth whitening fluid. Second supply port 204 that is an opening of element accommodating space 280 is opened in guiding surface 221, and surrounds a periphery of first supply port 203 through partition element 270.

Upper one of flanges 240 is formed at an upper edge of curved element 220 and projects into curved element 220. Lower one of flanges 240 is formed at a lower edge of curved element 220 and projects into curved element 220. A tip end of each flange 240 includes a rounded part.

Two rims 250 are opposed to each other across a gap in a direction of a center axis of barrel 230. Each of two ribs 260 is formed from the back surface of curved element 220 to rims 250 along the back surface of curved element 220 and a side surface of barrel 230.

Figure 10:
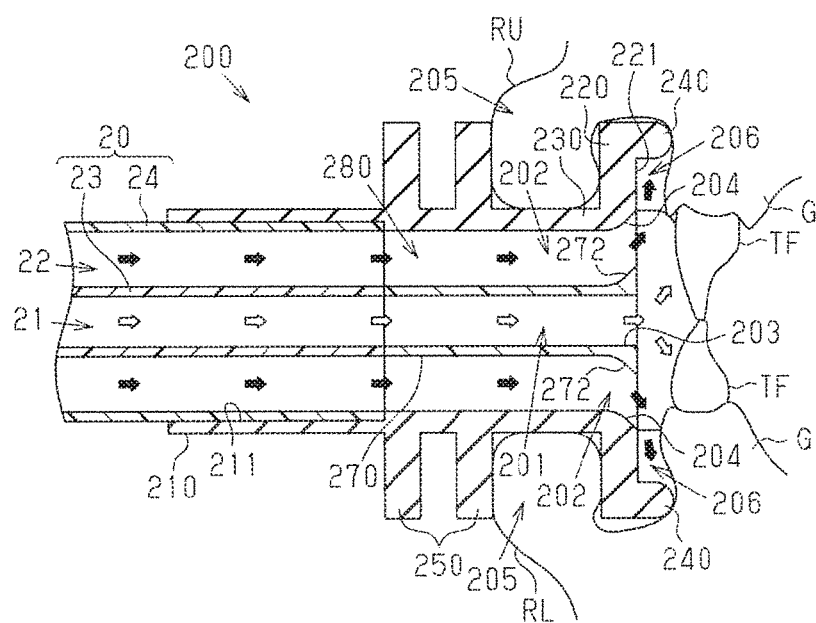
FIG. 10 is a sectional view of the mouthpiece according to the sixth exemplary embodiment.

Referring to FIG. 10, first supply port 203 is directed in a direction of the center axis of partition element 270. On the other hand, second supply port 204 is directed outward gradually from a side of connector 210 to a side of guiding surface 221 in a direction orthogonal to the center axis of partition element 270.

Figure 11:
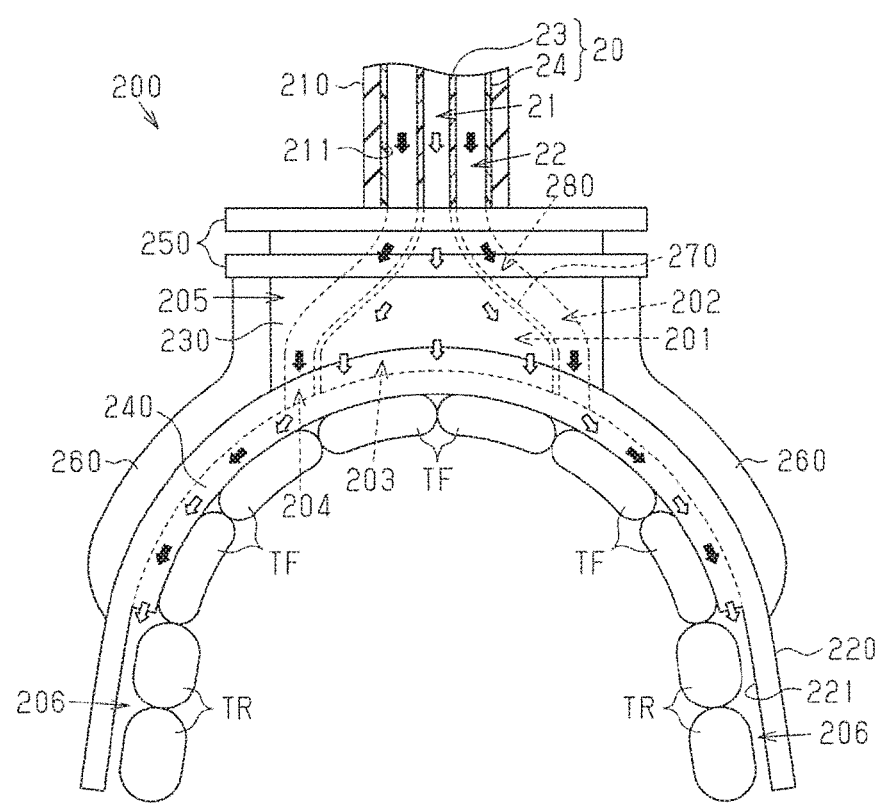
FIG. 11 is a plan view of the mouthpiece according to the sixth exemplary embodiment.

FIG. 11 shows a planar structure of mouthpiece 200.

One example of coupling part 20 is a hose including inner tube 23 and outer tube 24 in the same manner as the second exemplary embodiment. When coupling part 20 is inserted in connecting passage 211 of mouthpiece 200, passages of mouthpiece 200 and passages of coupling part 20 form the following connecting relationship. First supply passage 201 of mouthpiece 200 is in communication with first supply passage 21 of coupling part 20, and is not in communication with second supply passage 22 of coupling part 20. Second supply passage 202 of mouthpiece 200 is in communication with second supply passage 22 of coupling part 20, and is not in communication with first supply passage 21 of coupling part 20.

FIG. 10 shows a state in which mouthpiece 200 is placed in the oral cavity of the user.

The user holds mouthpiece 200 by arranging his or her upper lip RU in upper lip receiving space 205, his or her lower lip RL in lower lip receiving space 205, upper one of flanges 240 between his or her upper lip RU and gums G, and lower one of flanges 240 between his or her lower lip RL and gums G.

When mouthpiece 200 is placed in the oral cavity, curved element 220, barrel 230, one of rims 250, and two ribs 260 are respectively in contact with the upper lip RU and the lower lip RL. Upper one of flanges 240 contacts upper gums G to form guiding passage 206 between guiding surface 221 of curved element 220 and the upper teeth and gums G.

Lower one of flanges 240 contacts lower gums G to form guiding passage 206 between guiding surface 221 of curved element 220 and the lower teeth and gums G. The rounded part of each of flanges 240 gives soft touch to gums G.

Operation of teeth whitening device 10 is described below with reference to FIGS. 10 and 11.

As illustrated in FIG. 10, the teeth whitening fluid is supplied from first supply passage 21 of coupling part 20 to first supply passage 201 of mouthpiece 200. The teeth whitening fluid of first supply passage 201 is supplied from first supply port 203 to guiding passage 206. Thus, the teeth whitening fluid reaches front teeth TF or rear teeth TR and whitens the teeth.

The humidified gas is supplied from second supply passage 22 of coupling part 20 to second supply passage 202 of mouthpiece 200. The humidified gas of second supply passage 202 is supplied from second supply port 204 toward a direction of gums G through guiding passage 206. Thus, the humidified gas reaches upper gums G and lower gums G and suppresses drying of the organs.

As illustrated in FIG. 11, the teeth whitening fluid of guiding passage 206 is guided by guiding surface 221 of curved element 220 to flow in guiding passage 206 along the teeth. Thus, the teeth whitening fluid reaches substantially all of the upper teeth and the lower teeth and whitens the teeth.

The humidified gas of guiding passage 206 is guided by guiding surface 221 of curved element 220 to flow in guiding passage 206 along the teeth. Thus, the humidified gas reaches substantially all of upper gums G and lower gums G and suppresses drying of the organs.

Teeth whitening device 10 according to sixth exemplary embodiment has the following advantageous effects in addition to (1) to (19) achieved by teeth whitening device 10 according to the fifth exemplary embodiment.

(20) Mouthpiece 200 includes curved element 220 that is capable of forming guiding passage 206 between the upper teeth and the lower teeth. With this configuration, when the user places mouthpiece 200 in his or her oral cavity, the upper teeth and the lower teeth are simultaneously whitened. Thus, time required to whiten the teeth is shortened as compared to a case in which mouthpiece 200 does not include curved element 220.

(21) Second supply port 204 is directed differently from first supply port 203. With this configuration, the teeth whitening fluid and the humidified gas supplied from mouthpiece 200 to the oral cavity do not easily mix with each other. Thus, for example, possibility of deactivation caused by mixing active ingredients contained in the teeth whitening fluid with the humidified gas is reduced. As a result, the teeth are whitened efficiently as compared to a case in which first supply port 203 and second supply port 204 are directed in the same direction.

(22) Second supply port 204 is directed in a direction capable of supplying the humidified gas to gums G. With this configuration, the humidified gas supplied from second supply port 204 to the oral cavity easily reaches gums G. Thus, drying of gums G is efficiently suppressed as compared to a case in which second supply port 204 is directed differently from the above described direction.

Seventh Exemplary Embodiment

Figure 12:
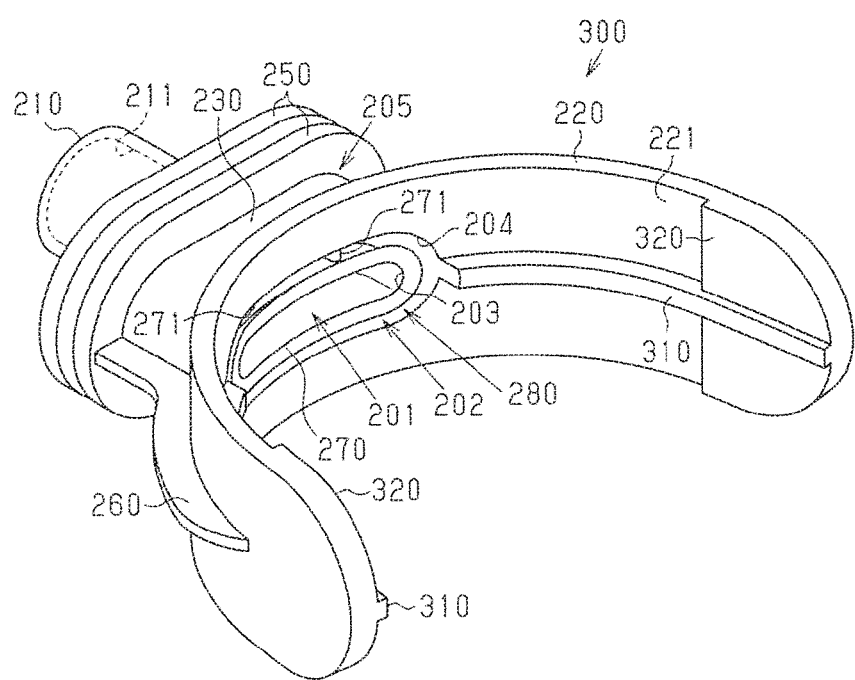
FIG. 12 is a perspective view of a mouthpiece according to a seventh exemplary embodiment.

A configuration of teeth whitening device 10 according to a seventh exemplary embodiment is described below with reference to FIGS. 12 and 13. Teeth whitening device 10 according to the seventh exemplary embodiment includes mouthpiece 300 shown in FIG. 12 instead of mouthpiece 100 of teeth whitening device 10 according to the first exemplary embodiment shown in FIG. 1.

Mouthpiece 300 includes connector 210, curved element 220, barrel 230, two rims 250, and two ribs 260 which are commonly used in mouthpiece 200 according to the sixth exemplary embodiment. Mouthpiece 300 also includes first supply passage 201, second supply passage 202, first supply port 203, and second supply port 204 which are commonly used in mouthpiece 200 according to the sixth exemplary embodiment. Differences between mouthpiece 300 and mouthpiece 200 according to the sixth exemplary embodiment are described below.

Mouthpiece 300 includes two occluded elements 310 projecting from curved element 220, and two thick portions 320 also projecting from curved element 220. Each of occluded elements 310 and each of thick portions 320 are curved in accordance with a shape of curved element 220.

One of occluded elements 310 is formed from one edge of first supply port 203 to one end of curved element 220 and projects from guiding surface 221 toward an inside of curved element 220. The other one of occluded elements 310 is formed from the other edge of first supply port 203 to the other end of curved element 220, and projects from guiding surface 221 toward the inside of curved element 220.

One of thick portions 320 is formed at one end of curved element 220 and projects from guiding surface 221 toward the inside of curved element 220. The other one of thick portions 320 is formed at the other end of curved element 220, and projects from guiding surface 221 toward the inside of curved element 220.

Figure 13:
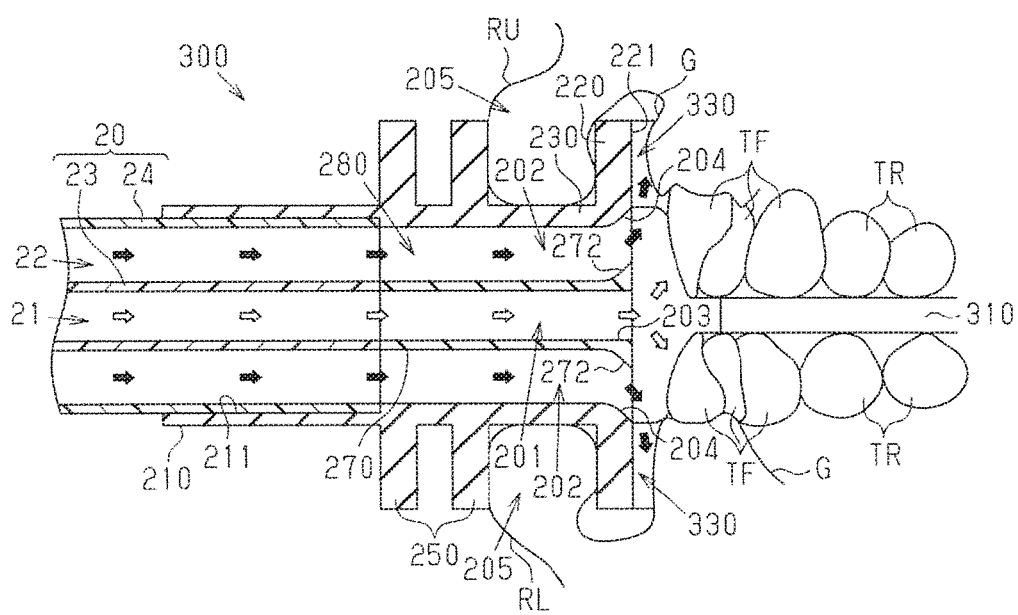
FIG. 13 is a sectional view of the mouthpiece according to the seventh exemplary embodiment.

FIG. 13 shows a state in which mouthpiece 300 is placed in the oral cavity of the user.

The user holds mouthpiece 300 by biting occluded elements 310 with his or her upper teeth and lower teeth respectively. When mouthpiece 300 is placed in the oral cavity, an upper part of guiding surface 221 above occluded elements 310 forms guiding passage 330 with surfaces of the upper teeth and the upper gums G. A lower part of guiding surface 221 below occluded elements 310 forms guiding passage 330 with surfaces of the lower teeth and the lower gums G.

Thick portions 320 come in contact respectively with upper gums G at the roots of the first molar and the second molar, and with lower gums G at the roots of the first molar and the second molar. Thus, a state in which guiding passage 330 is formed is easily maintained.

Operation of teeth whitening device 10 is described below with reference to FIG. 13.

The teeth whitening fluid is supplied from first supply passage 21 of coupling part 20 to first supply passage 201 of mouthpiece 300. The teeth whitening fluid of first supply passage 201 is supplied from first supply port 203 to guiding passage 330. The humidified gas is supplied from second supply passage 22 of coupling part 20 to second supply passage 202 of mouthpiece 300. The humidified gas of second supply passage 202 is supplied from second supply port 204 to guiding passage 330 in a direction of gums G. Flows of the teeth whitening fluid and the humidified gas supplied to guiding passage 330 are substantially the same as the flows of the teeth whitening fluid and the humidified gas of guiding passage 206 according to the sixth exemplary embodiment.

Teeth whitening device 10 according to seventh exemplary embodiment has the following advantageous effects in addition to (1) to (22) achieved by teeth whitening device 10 according to the sixth exemplary embodiment.

(23) Mouthpiece 300 includes occluded elements 310. With this configuration, guiding passage 330 formed between guiding surface 221 and the upper teeth and guiding passage 330 formed between guiding surface 221 and the lower teeth are partitioned by occluded elements 310. Thus, a flow of the teeth whitening fluid is formed along each of the upper teeth and the lower teeth, and thus the teeth whitening fluid stably flows along the teeth as compared to a case in which mouthpiece 300 does not include occluded elements 310.

Eighth Exemplary Embodiment

A configuration of teeth whitening device 10 according to an eighth exemplary embodiment is described below with reference to FIGS. 14 and 15. Teeth whitening device 10 according to the eighth exemplary embodiment includes coupling part 60 and mouthpiece 400 shown in FIG. 14 instead of coupling part 20 and mouthpiece 100 of teeth whitening device 10 according to the first exemplary embodiment shown in FIG. 1. Note that teeth whitening device 10 according to the eighth exemplary embodiment has advantageous effects similar to those of mouthpiece 200 according to the sixth exemplary embodiment.

Coupling part 60 includes two tubular objects, first coupling part 63 and second coupling part 64.

In the illustrated example, first coupling part 63 and second coupling part 64 are formed integrally. First coupling part 63 includes first supply passage 61 that is configured to guide the teeth whitening fluid supplied from generator 30 to mouthpiece 400. Second coupling part 64 includes second supply passage 62 that is configured to guide the humidified gas supplied from generator 30 to mouthpiece 400. First supply passage 61 and second supply passage 62 are separated from each other in such a manner that the fluids flowing in the passages do not mix each other.

Housing 34 includes first connector 35A connected with first coupling part 63, and second connector 35B connected with second coupling part 64. First connector 35A includes first connecting passage 36A that allows first supply passage 31 of generator 30 to communicate with an outside of generator 30. Second connector 35B includes second connecting passage 36B that allows second supply passage 32 of generator 30 to communicate with the outside of generator 30.

When coupling part 60 is inserted in first connector 35A and second connector 35B of generator 30, passages of generator 30 and passages of coupling part 60 form a following connecting relationship. First supply passage 31 of generator 30 is in communication with first supply passage 61 of first coupling part 63, and is not in communication with second supply passage 62 of second coupling part 64. Second supply passage 32 of generator 30 is in communication with second supply passage 62 of second coupling part 64, and is not in communication with first supply passage 61 of first coupling part 63.

Mouthpiece 400 is different from mouthpiece 200 according to the sixth exemplary embodiment regarding the following points, and has substantially the same configuration as mouthpiece 200 according to the sixth exemplary embodiment except the following points. Mouthpiece 400 includes connector 410 instead of connector 210 of mouthpiece 200, and partition element 440 instead of partition element 270 of mouthpiece 200. Mouthpiece 400 further includes first supply port 403 instead of first supply port 203, second supply port 404 instead of second supply port 204, first supply passage 401 instead of first supply passage 201, and second supply passage 402 instead of second supply passage 202.

In one example, connector 410, curved element 220, barrel 230, two flanges 240, two rims 250, and two ribs 260 are integrally formed resin elements, and partition element 440 is another resin element differently formed from the integrally formed resin elements.

Connector 410 includes first connector 420 connected with first coupling part 63, and second connector 430 connected with second coupling part 64. First connector 420 includes first connecting passage 421 that allows element accommodating space 280 of barrel 230 to communicate with an outside of mouthpiece 400. Second connector 430 includes second connecting passage 431 that allows element accommodating space 280 of barrel 230 to communicate with the outside of mouthpiece 400.

When coupling part 60 is inserted in connector 410 of mouthpiece 400, the passages of mouthpiece 400 and the passages of coupling part 60 form a following connecting relationship. First supply passage 401 of mouthpiece 400 is in communication with first supply passage 61 of first coupling part 63, and is not in communication with second supply passage 62 of second coupling part 64. Second supply passage 402 of mouthpiece 400 is in communication with second supply passage 62 of second coupling part 64, and is not in communication with first supply passage 61 of first coupling part 63.

Figure 15:
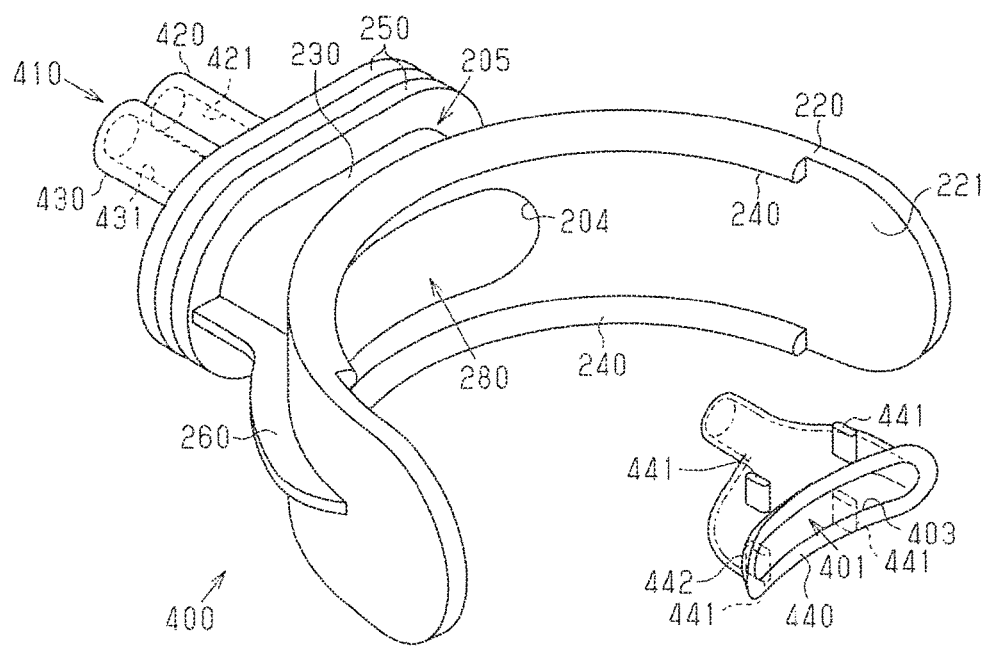
FIG. 15 is an exploded perspective view of a mouthpiece according to the eighth exemplary embodiment.

FIG. 15 shows a structure of mouthpiece 400 in an exploded perspective view.

Partition element 440 includes a plurality of supporting projections 441 configured to hold a shape of partition element 440 in such a manner that second supply passage 402 is formed between an inner surface of barrel 230 and an inner surface of curved element 220, first supply passage 401, and first supply port 403. Partition element 440 further includes inclined part 442 that directs second supply port 404 to a direction different from first supply port 403. Inclined part 442 includes substantially the same configuration as inclined part 272 according to the sixth exemplary embodiment.

Partition element 440 is inserted in element accommodating space 280 and supporting projections 441 are firmly attached to the inner surface of barrel 230. As a result, partition element 440 is fixed to barrel 230 to form mouthpiece 400 as shown in FIG. 14.

Figure 14:
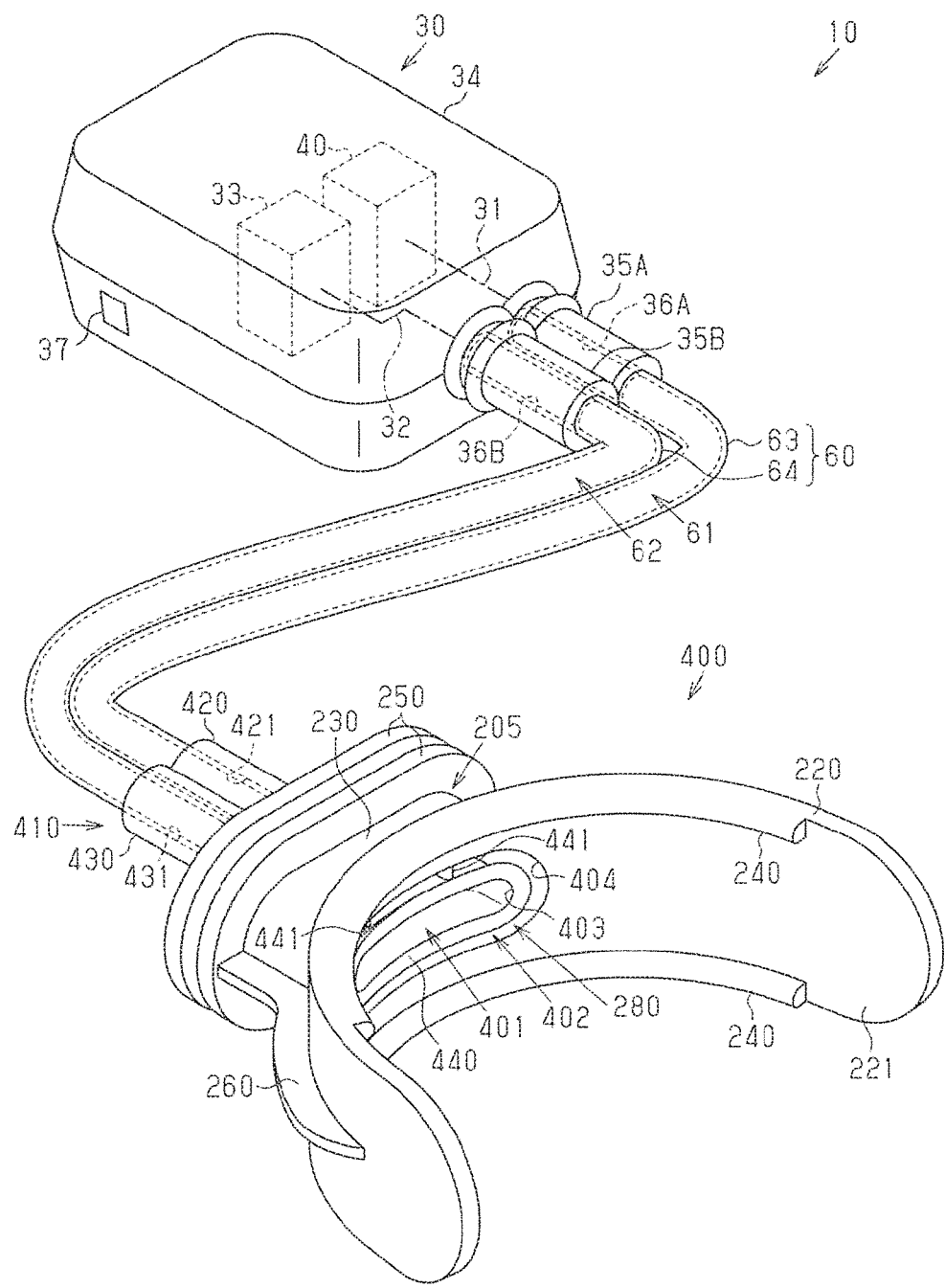
FIG. 14 is a perspective view of a teeth whitening device according to an eighth exemplary embodiment.

As illustrated in FIG. 14, in mouthpiece 400, element accommodating space 280 is partitioned by partition element 440, and second supply passage 402 and second supply port 404 are formed by a part of element accommodating space 280 surrounded by the inner surface of barrel 230, the inner surface of curved element 220, and an outer surface of partition element 440. First supply passage 401 allows first connecting passage 421 to communicate with first supply port 403. Second supply passage 402 allows second connecting passage 431 to communicate with second supply port 404. Second supply port 404, which is an opening of element accommodating space 280, is opened in guiding surface 221, and surrounds a periphery of first supply port 403 through partition element 440.

Figure 16:
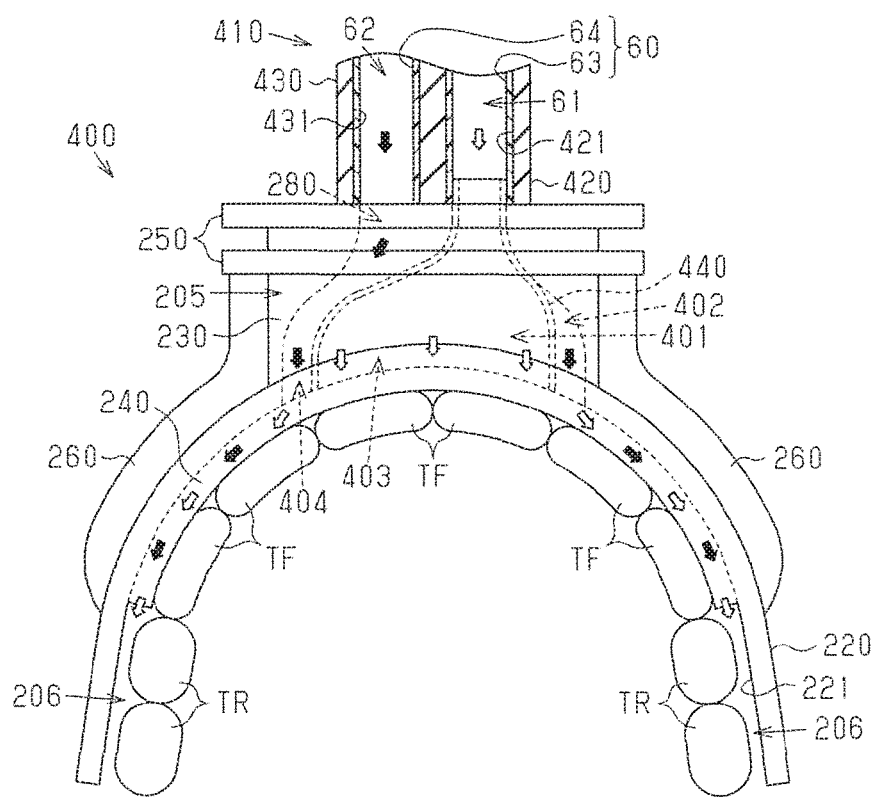
FIG. 16 is a plan view of the mouthpiece according to the eighth exemplary embodiment.

Operation of teeth whitening device 10 is described below with reference to FIG. 16.

The teeth whitening fluid is supplied from first supply passage 61 of coupling part 60 to first supply passage 401 of mouthpiece 400. The teeth whitening fluid of first supply passage 401 is supplied from first supply port 403 to guiding passage 206. The humidified gas is supplied from second supply passage 62 of coupling part 60 to second supply passage 402 of mouthpiece 400. The humidified gas of second supply passage 402 is supplied from second supply port 404 to guiding passage 206 toward gums G. Flows of teeth whitening fluid and the humidified gas supplied to guiding passage 206 are substantially the same as the flows of the teeth whitening fluid and the humidified gas of guiding passage 206 according to the sixth exemplary embodiment.

Ninth Exemplary Embodiment

A configuration of teeth whitening device 10 according to a ninth exemplary embodiment is described below with reference to FIGS. 17 to 19B. Note that FIGS. 19A and 19B are sectional views taken along lines Z19A-Z19A and Z19B-Z19B in FIG. 18 respectively. In FIGS. 19A and 19B, the teeth (TF, TR) and the gums (G) are also illustrated for easy understanding. Teeth whitening device 10 according to the ninth exemplary embodiment includes mouthpiece 500 shown in FIG. 17, instead of mouthpiece 100 of teeth whitening device 10 according to the first exemplary embodiment shown in FIG. 1.

Mouthpiece 500 has, for example, a symmetrical shape with respect to a center line in a lateral direction in a plan view and can have various sizes according to the user's age or the like. One example of a material forming mouthpiece 500 is a silicone rubber.

Mouthpiece 500 includes connector 510 connected with coupling part 20 (see FIG. 18), outer curved element 520 curved to guide a flow of the teeth whitening fluid, and hollow barrel 530 that connects connector 510 and outer curved element 520. Mouthpiece 500 further includes two flanges 540 projecting from outer curved element 520, two rims 550 projecting from the periphery of barrel 530, occluded element 560 projecting from outer curved element 520, and inner curved element 570 projecting from occluded element 560. One example of barrel 530 is an oval tube. Each of flanges 540, occluded element 560, and inner curved element 570 are curved in accordance with a shape of outer curved element 520.

Mouthpiece 500 further includes teeth receiving space 505, an upper part of lip receiving space 507, and a lower part of lip receiving space 507. Teeth receiving space 505 is formed by being surrounded by outer curved element 520, occluded element 560, and inner curved element 570. The upper part of lip receiving space 507 is formed by being surrounded by a back surface of outer curved element 520, a top surface of barrel 530, and a side surface of one of rims 550. The lower part of lip receiving space 507 is formed by being surrounded by the back surface of outer curved element 520, a bottom surface of barrel 530, and the side surface of one of rims 550.

As illustrated in 19A, mouthpiece 500 further includes first supply passage 501, second supply passage 502, two first supply ports 503, and two second supply ports 504. First supply passage 501 includes inlet passage 50A formed inside of outer curved element 520 and barrel 530, and outlet passage 50B formed inside of occluded element 560. Second supply passage 502 is formed inside of outer curved element 520 and barrel 530. First supply port 503 allows outlet passage 50B that is an inner space of mouthpiece 500 to communicate with an outside of mouthpiece 500. Second supply port 504 allows second supply passage 502 that is an inner space of mouthpiece 500 to communicate with the outside of mouthpiece 500.

Figure 17:
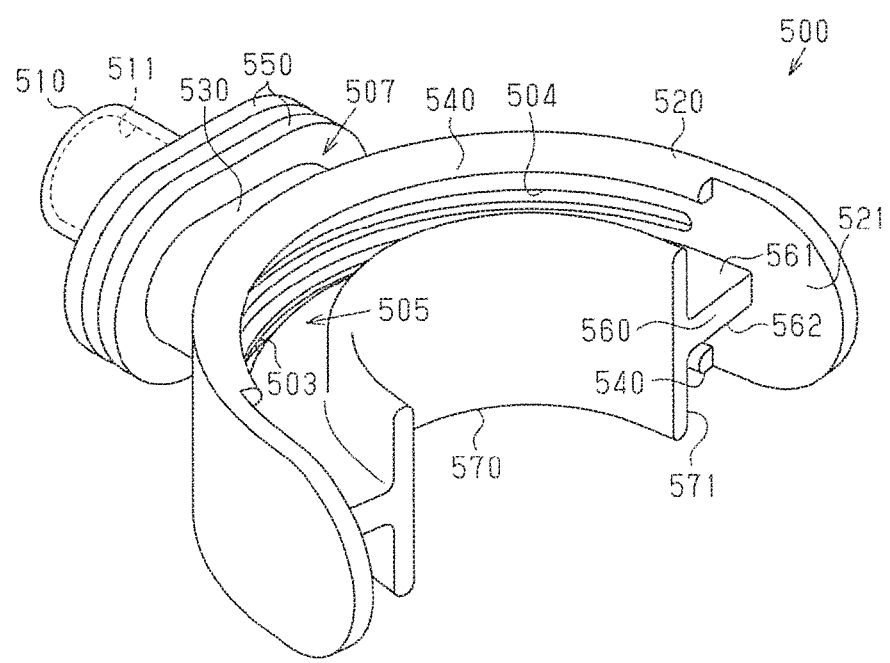
FIG. 17 is a perspective view of a mouthpiece according to a ninth exemplary embodiment.
Figure 18:
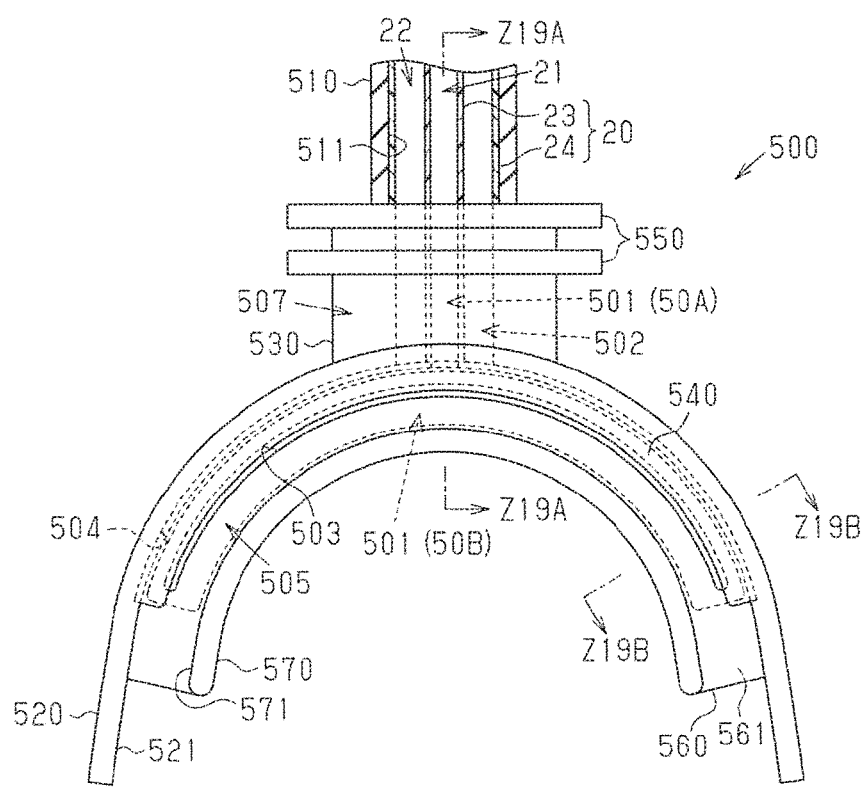
FIG. 18 is a plan view of the mouthpiece according to the ninth exemplary embodiment.
Figure 19A:
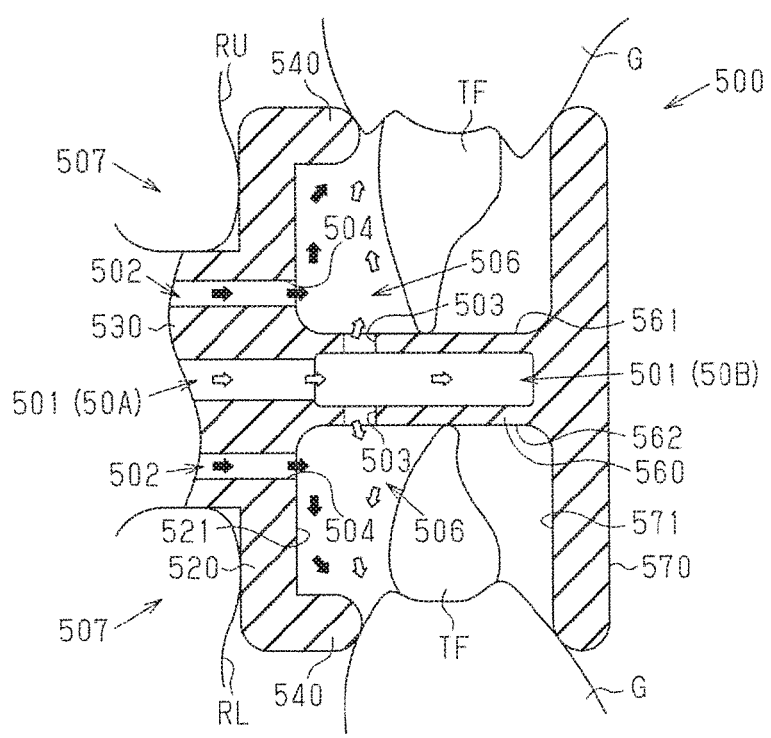
FIG. 19A is a sectional view taken along line Z19A-Z19A in FIG. 18.
Figure 19B:
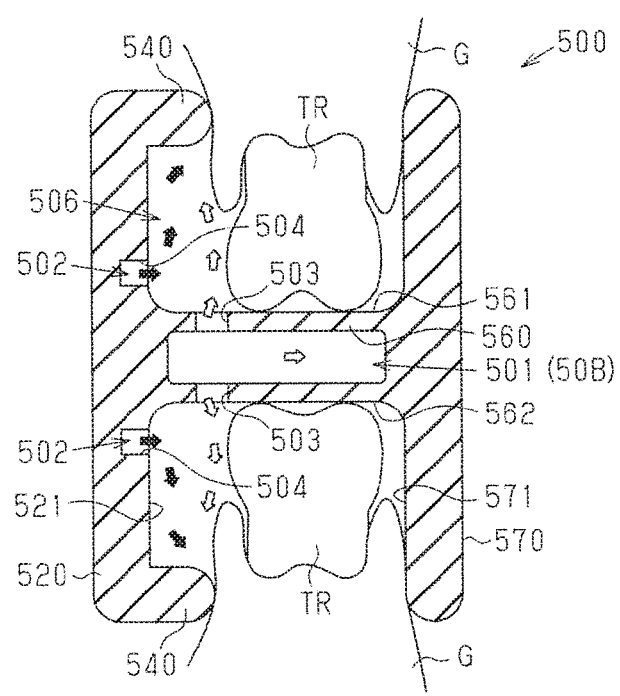
FIG. 19B is a sectional view taken along line Z19B-Z19B in FIG. 18.

As illustrated in FIGS. 17 and 18, outlet passage 50B and first supply port 503 are formed in an extending direction of, for example, occluded element 560. Second supply port 504 is formed in an extending direction of, for example, outer curved element 520.

As illustrated in FIG. 18, connector 510 includes connecting passage 511 that allows inlet passage 50A and second supply passage 502 to communicate with the outside of mouthpiece 500. First supply passage 501 allows connecting passage 511 to communicate with first supply port 503. Second supply passage 502 allows connecting passage 511 to communicate with second supply port 504.

As illustrated in FIG. 17, outer curved element 520 includes guiding surface 521 that is configured to guide the teeth whitening fluid. One of second supply ports 504 is opened in an upper part of guiding surface 521 above occluded element 560. The other one of second supply ports 504 (see FIG. 19A) is opened in a lower part of guiding surface 521 below occluded element 560.

Upper one of flanges 540 is formed at an upper edge of outer curved element 520, and projects inwardly from outer curved element 520. Lower one of flanges 540 is formed at a lower edge of outer curved element 520, and projects inwardly from outer curved element 520. A tip end of each flange 540 includes a rounded part. Two rims 550 are opposed to each other across a gap in a direction of the center axis of barrel 530.

Occluded element 560 includes upper surface 561 and lower surface 562 that relatively have a front/back relationship and project toward an inside of outer curved element 520. Inner curved element 570 is an element projecting from upper surface 561 of occluded element 560 in a height direction of mouthpiece 500, and includes guiding surface 571 that faces guiding surface 521 of outer curved element 520.

As illustrated in FIGS. 19A and 19B, upper one of first supply ports 503 is opened in upper surface 561 of occluded element 560, lower one of first supply ports 503 is opened in lower surface 562 of occluded element 560. Upper one of first supply ports 503 and lower one of first supply ports 503 are opposed to each other across outlet passage 50B formed inside occluded element 560. A flow passage area of outlet passage 50B is larger than that of first supply passage 21 of coupling part 20, that of inlet passage 50A, and that of first supply port 503.

A position of first supply port 503 of occluded element 560 is set close to outer curved element 520 in a direction in which occluded element 560 projects from guiding surface 521 of outer curved element 520.

FIG. 18 shows a structure of mouthpiece 500 in a plan view.

One example of coupling part 20 is a hose including inner tube 23 and outer tube 24 in the same manner as the second exemplary embodiment. When coupling part 20 is inserted in connecting passage 511 of mouthpiece 500, passages of mouthpiece 500 and passages of coupling part 20 form a following connecting relationship. First supply passage 501 of mouthpiece 500 is in communication with first supply passage 21 of coupling part 20, and is not in communication with second supply passage 22 of coupling part 20. Second supply passage 502 of mouthpiece 500 is in communication with second supply passage 22 of coupling part 20, and is not in communication with first supply passage 21 of coupling part 20.

FIG. 19A shows front teeth TF and surroundings of front teeth TF in the oral cavity of the user in which mouthpiece 500 is placed. FIG. 19B shows rear teeth TR and surroundings of rear teeth TR in the oral cavity of the user in which mouthpiece 500 is placed.

A height of teeth receiving space 505 is set, for example, in such a manner that the roots of front teeth TF and rear teeth TR that are in contact with gums G are accommodated in teeth receiving space 505. Note that the height of teeth receiving space 505 is equal to a distance between an upper surface 561 of occluded element 560 and a top surface of outer curved element 520 or a top surface of inner curved element 570.

A width of teeth receiving space 505 is set, for example, in such a manner that guiding passage 506 that is a gap having an appropriate size is formed between guiding surface 521 of outer curved element 520 and front teeth TF and between guiding surface 521 and rear teeth TR. Note that the width of teeth receiving space 505 is a distance between guiding surface 521 of outer curved element 520 and guiding surface 571 of inner curved element 570 in a direction in which occluded element 560 projects from guiding surface 521.

A width of an opening of teeth receiving space 505 is set, for example, in such a manner that guiding surface 521 of outer curved element 520 and guiding surface 571 of inner curved element 570 contact with an appropriate pressure with the roots of front teeth TF and rear teeth TR in gums G. Note that the width of the opening of teeth receiving space 505 is a distance between the tip end of flanges 540 and guiding surface 571 of inner curved element 570 in a direction in which occluded element 560 projects from guiding surface 521.

As illustrated in FIG. 19A, when mouthpiece 500 is placed in the oral cavity, the upper lip RU is placed in the upper part of lip receiving space 507 and the lower lip RL is placed in the lower part of lip receiving space 507. The incisal edges of upper front teeth TF is in contact with upper surface 561 of occluded element 560, and the incisal edges of lower front teeth TF is in contact with lower surface 562 of occluded element 560.

Guiding surface 521 of outer curved element 520 forms guiding passage 506 with front teeth TF. Upper one of flanges 540 comes in contact with a surface of the roots of upper front teeth TF at gums G. Lower one of flanges 540 makes firm contact with a front surface of the roots of lower front teeth TF at gums G. Guiding surface 571 of inner curved element 570 makes firm contact with a back surface of the roots of upper front teeth TF at gums G and the back surface of the roots of lower front teeth TF at gums G. The rounded part of each of flanges 540 gives soft touch to gums G.

As illustrated in FIG. 19B, when mouthpiece 500 is placed in the oral cavity, the occlusal surface of upper rear teeth TR contacts upper surface 561 of occluded element 560, and occlusal surface of lower rear teeth TR contacts lower surface 562 of occluded element 560.

Guiding surface 521 of outer curved element 520 forms guiding passage 506 with rear teeth TR. Upper one of flanges 540 makes firm contact with a front surface of the roots of upper rear teeth TR at gums G. Lower one of flanges 540 makes firm contact with a front surface of lower rear teeth TR at gums G. Guiding surface 571 of inner curved element 570 makes firm contact with a back surface of the roots of upper rear teeth TR at gums G and the back surface of the roots of lower rear teeth TR at gums G.

Operation of teeth whitening device 10 is described below with reference to FIGS. 19A and 19B.

As illustrated in FIG. 19A, the teeth whitening fluid is supplied from first supply passage 21 of coupling part 20 to inlet passage 50A which is first supply passage 501 of mouthpiece 500. The flow speed of the teeth whitening fluid of first supply passage 501 is lowered when the teeth whitening fluid flows in outlet passage 50B from inlet passage 50A. The teeth whitening fluid of outlet passage 50B is supplied to guiding passage 506 from an intermediate part of first supply port 503. Thus, the teeth whitening fluid reaches front teeth TF and whitens the teeth.

The humidified gas is supplied from second supply passage 22 of coupling part 20 to second supply passage 502 of mouthpiece 500. The humidified gas of second supply passage 502 is supplied to guiding passage 506 from an intermediate part of second supply port 504. Thus, the humidified gas reaches gums G at the roots of front teeth TF, and suppresses drying of the organs.

As illustrated in FIG. 19B, the teeth whitening fluid of first supply passage 501 is supplied to guiding passage 506 from a part nearer to the end than the intermediate part of first supply port 503. Thus, the teeth whitening fluid reaches rear teeth TR and whitens the teeth.

The humidified gas of second supply passage 502 is supplied to guiding passage 506 from a part nearer to the end than the intermediate part of second supply port 504. Thus, the humidified gas reaches gums G at the roots of rear teeth TR and suppresses drying of the organs.

The teeth whitening fluid of guiding passage 506 is guided by guiding surface 521 of outer curved element 520 to flow in guiding passage 506 along the teeth. Thus, the teeth whitening fluid reaches substantially all of the upper teeth and the lower teeth and whitens the teeth. The humidified gas of guiding passage 506 is guided by guiding surface 521 of outer curved element 520 to flow in guiding passage 506 along the teeth. With this configuration, the humidified gas reaches substantially all of upper gums G and lower gums G to suppress drying of the organs.

Teeth whitening device 10 according to the ninth exemplary embodiment has the following advantageous effects in addition to (1) to (12) and (14) to (23) achieved by teeth whitening device 10 according to the eighth exemplary embodiment.

(24) In mouthpiece 500, outlet passage 50B is formed inside occluded element 560, and first supply port 503 is opened in each of upper surface 561 and lower surface 562 of occluded element 560. With this configuration, the flow direction of the teeth whitening fluid greatly changes when the teeth whitening fluid in mouthpiece 500 passes through outlet passage 50B and first supply port 503. Thus, the teeth whitening fluid tends to stay in outlet passage 50B. Accordingly, the active ingredients in outlet passage 50B are easily diffused into the teeth whitening fluid. As a result, the teeth whitening fluid having small variations in concentration of the active ingredients is supplied from first supply port 503 to guiding passage 506. Thus, differences in degree of whitening in each portion of one tooth and in degree of whitening between the teeth are hardly generated.

(25) Outlet passage 50B is formed inside occluded element 560. With this configuration, the thickness of outer curved element 520 can be set thinner as compared to a case in which a passage having the same volume as outlet passage 50B is formed inside outer curved element 520. The user can easily put on mouthpiece 500 in a case where the thickness of outer curved element 520 is set thinner.

Modified Examples

The description of each of the above embodiments illustrates an embodiment of the teeth whitening device of the present invention and is not considered to be restrictive. In addition to each of the embodiments, the teeth whitening device of the present invention may include, for example, the following modified examples of each embodiment.

According to a modified example of coupling part 20 of the first to fifth exemplary embodiments, first supply passage 21 of coupling part 20 is directly connected with first supply port 103 of mouthpiece 100. Note that coupling part 20, 60 according to the second to ninth exemplary embodiments can be modified in the same manner.

According to a modified example of coupling part 20 of first to fifth exemplary embodiments, second supply passage 22 of coupling part 20 is directly connected with second supply port 104 of mouthpiece 100. Note that coupling part 20, 60 according to the second to ninth exemplary embodiments can be modified in the same manner.

According to a modified example of mouthpiece 100 of the first to fifth exemplary embodiments, a plurality of first supply ports 103 and a plurality of second supply port 104 are formed.

A modified example of teeth whitening device 10 according to the first to fifth exemplary embodiments includes two mouthpieces 100 and two coupling parts 20. One of mouthpieces 100 is used to whiten the upper teeth. The other one of mouthpieces 100 is used to whiten the lower teeth. One of mouthpieces 100 is connected with generator 30 through one of coupling parts 20. The other one of mouthpieces 100 is joined with generator 30 with the other one of coupling part 20. According to teeth whitening device 10 of this modified example, the upper teeth and the lower teeth can be simultaneously whitened when the user puts both of two mouthpieces 100.

Teeth whitening device 10 according to a further modified example includes a common coupling part that connects two mouthpieces 100 with generator 30, instead of two coupling parts 20.

A modified example of teeth whitening device 10 according to the fourth exemplary embodiment includes a manual air pump instead of the electric air pump 55.

A modified example of generator 30 according to the fourth exemplary embodiment includes a primary battery or a secondary battery instead of power supply 51.

A modified example of resonant circuit 53 according to the fourth exemplary embodiment includes a circuit configuration in which a secondary electrode of laminated piezoelectric transformer 54, a reactor, and atomization electrode 41 of discharger 40 are connected in series.

A modified example of discharger 40 according to the fifth exemplary embodiment includes a device configured to condense water on atomization electrode 41 or a device configured to supply water to atomization electrode 41, instead of cooling module 44.

In a modified example of mouthpiece 200 according to the sixth exemplary embodiment, inclined part 272 is formed on an inner peripheral surface of partition element 270. In this case, first supply port 203 is directed inward in a direction orthogonal to a center axis of partition element 270 from a side of connector 210 to a side of guiding surface 221 in a direction of the center axis. With this configuration, the teeth whitening fluid supplied from first supply port 203 to guiding passage 206 is not easily mixed with the humidified gas supplied from second supply port 204 to guiding passage 206.

A modified example of mouthpiece 200 according to the sixth exemplary embodiment includes a first supply port and a second supply port having a shape similar to a rectangular, instead of first supply port 203 and second supply port 204. The first supply port is formed to extend in an extending direction of curved element 220, and is opened in guiding surface 221 at a position capable of facing the teeth to supply the teeth whitening fluid into the oral cavity. The second supply port is formed to extend in an extending direction of curved element 220, and is opened in guiding surface 221 at a position capable of facing the gums to supply the humidified gas into oral cavity.

In a modified example of mouthpiece 500 according to the ninth exemplary embodiment, occluded element 560 includes a plurality of first supply ports 503.

In a modified example of mouthpiece 500 according to the ninth exemplary embodiment, a part of outer curved element 520 and a part of inner curved element 570 that are configured to form a lower side of teeth receiving space 505 and a lower side of first supply port 503 are omitted. According to this modified example, the user can use the mouthpiece to whiten only his or her upper teeth.

In a modified example of mouthpiece 500 according to the ninth exemplary embodiment, a part of outer curved element 520 and a part of inner curved element 570 that are configured to form the upper side of teeth receiving space 505 and the upper side of first supply port 503 are omitted. According to this modified example, the user can use the mouthpiece to whiten only his or her lower teeth.

In modified examples of mouthpieces 100, 200, 300, 400, 500 according to the exemplary embodiments, mouthpieces are formed from a plastic material other than silicone rubber. The material is, for example, elastomer rubber, flexible polyvinyl chloride, or ethylene propylene diene rubber.

A modified example of generator 30 according to each exemplary embodiment supplies DC power to discharger 40 to allow discharger 40 to generate discharge.

A modified example of generator 30 according to each exemplary embodiment generates discharge in a form other than corona discharge, such as glow discharge or arc discharge.

A modified example of generator 30 according to each exemplary embodiment generates the teeth whitening fluid in a form of plasma.

A modified example of teeth whitening device 10 according to each exemplary embodiment further includes a first generator including discharger 40 and a second generator including humidifier 33, instead of generator 30. Teeth whitening device 10 according to this modified example includes a coupling part that couples the first generator and the second generator with each of mouthpiece 100, 200, 300, 400, 500, instead of coupling part 20.

In a modified example of teeth whitening device 10 according to each exemplary embodiment, coupling part 20, 60 is integrated with at least one of generator 30 and mouthpiece 100, 200, 300, 400, 500.

In a modified example of teeth whitening device 10 according to each exemplary embodiment, generator 30 is directly connected with mouthpiece 100, 200, 300, 400, 500.

A modified example of teeth whitening device 10 according to each exemplary embodiment supplies the humidified gas to discharger 40 by humidifier 33, generates the teeth whitening fluid by using the gas, and supplies the teeth whitening fluid from generator 30 to mouthpiece 100, 200, 300, 400, 500. When this modified example is combined with the first exemplary embodiment, one of two supply passages included in each of generator 30, coupling part 20, and mouthpiece 100 can be omitted. Note that one of two supplying passage can also be omitted when the above modified example is combined with another exemplary embodiment.

A modified example of teeth whitening device 10 according to each exemplary embodiment supplies the teeth whitening fluid generated by discharger 40 to humidifier 33, generates the humidified gas by using the fluid, and supplies the humidified gas from generator 30 to mouthpiece 100, 200, 300, 400, 500. When the modified example is combined with the first exemplary embodiment, one of two supply passages included in each of generator 30, coupling part 20, and mouthpiece 100 can be omitted. Note that one of two supplying passages can also be omitted when the above modified example is combined with other exemplary embodiment.

The foregoing detailed description is to be considered as illustrative and not restrictive. For example, the above embodiments or one or more of the modified examples may be used in combination with each other. The technical features and subject matter of the present invention may be included in fewer features than all of the disclosed features of the specific embodiments. Accordingly, the claims are incorporated in the detailed description and each claim asserts itself as an individual embodiment. The scope of the present invention and equivalence of the present invention are to be understood with reference to the appended claims.

An Example of Teeth Whitening Device (1) A teeth whitening device according to one embodiment of the present invention includes a generator configured to generate a teeth whitening fluid that whitens teeth and humidified gas, and a mouthpiece including a supply port through which the teeth whitening fluid and the humidified gas generated by the generator are supplied.

With this teeth whitening device, a user places the mouthpiece that is an object to supply the teeth whitening fluid into his or her oral cavity, to hold the object at a position suitable for whitening the teeth. In other words, the user can whiten his or her teeth without holding the object that supplies the teeth whitening fluid with his or her hand. Therefore, the teeth whitening device can provide usability. In addition, the humidified gas is supplied from the mouthpiece to the oral cavity, and thus the oral cavity is not easily dried even if the user does not particularly supply water to his or her oral cavity. This also increases the usability of the teeth whitening device.

(2) According to one embodiment of the teeth whitening device, the mouthpiece includes a first supply port that is the supply port through which the teeth whitening fluid is supplied, and a second supply port that is the supply port through which the humidified gas is supplied, the second supply port being formed separately from the first supply port.

With this teeth whitening device, the teeth whitening fluid and the humidified gas are not easily mixed with each other before being supplied to the oral cavity. Thus, possibility of deactivation caused by mixing active ingredients contained in the teeth whitening fluid with the humidified gas is reduced. As a result, the teeth can be whitened efficiently as compared to a case in which the mouthpiece does not include the first supply port and the second supply port that are separated from each other.

(3) According to one embodiment of the teeth whitening device, the mouthpiece further includes a first supply passage configured to guide the teeth whitening fluid to the first supply port, and a second supply passage configured to guide the humidified gas to the second supply port, the second supply passage being formed separately from the first supply passage.

With this teeth whitening device, the teeth whitening fluid and the humidified gas are hardly mixed with each other when passing through the mouthpiece. Thus, for example, possibility of deactivation caused by mixing active ingredients contained in the teeth whitening fluid with the humidified gas is further reduced. As a result, the teeth can be whitened efficiently as compared to a case in which the mouthpiece does not include the first supply passage and the second supply passages that are separated from each other.

(4) According to one embodiment of the teeth whitening device, the first supply port and the second supply port are directed differently from each other.

With this teeth whitening device, the teeth whitening fluid and the humidified gas supplied from the mouthpiece to the oral cavity do not easily mix with each other. Thus, for example, possibility of deactivation caused by mixing active ingredients contained in the teeth whitening fluid with the humidified gas is reduced. As a result, the teeth can be whitened efficiently as compared to a case in which the first supply port and the second supply port are directed in the same direction.

(5) Another teeth whitening device according to one embodiment of the present invention includes a generator configured to generate humidified gas and generate from the humidified gas a teeth whitening fluid that whitens teeth, or a generator configured to generate a teeth whitening fluid that whitens the teeth and generate a humidified gas from the fluid, and a mouthpiece including a supply port through which the teeth whitening fluid or the humidified gas generated by the generator is supplied.

With this teeth whitening device, a user places the mouthpiece that is an object to supply the teeth whitening fluid into his or her oral cavity, to hold the object at a position suitable for whitening the teeth. In other words, the user can whiten his or her teeth without holding the object that supplies the teeth whitening fluid with his or her hand. Therefore, the teeth whitening device can provide usability. In addition, the humidified gas is supplied from the mouthpiece to the oral cavity, and thus the oral cavity is not easily dried even if the user does not particularly supply water to his or her oral cavity. This also increases the usability of the teeth whitening device.

(6) According to one embodiment of the teeth whitening device, the mouthpiece includes a curved element on which a guiding surface configured to guide the teeth whitening fluid is formed.

With this teeth whitening device, the teeth whitening fluid supplied to the oral cavity is guided by the guiding surface of the curved element and thus easily flows along the teeth. Accordingly, the teeth are efficiently whitened as compared to a case in which the mouthpiece does not include the curved element.

(7) According to one embodiment of the teeth whitening device, the supply port is opened in the guiding surface.

This teeth whitening device allows the teeth whitening fluid supplied from the supply port to the oral cavity to easily reach the teeth. Thus, the teeth are efficiently whitened compared to a case in which the supply port is not opened in the guiding surface. This teeth whitening device also allows the humidified gas supplied from the supply port to the oral cavity to easily reach the teeth. Thus, the gums are efficiently prevented from being dried as compared to a case in which the supply port is not opened in the guiding surface.

(8) According to one embodiment of the invention, the teeth whitening device further includes a coupling part that couples the generator with the mouthpiece, the coupling part includes a supply passage that directly or indirectly communicates with the supply port.

With this teeth whitening device, the user can insert the mouthpiece away from the generator, and thus the user can whiten the teeth in a relatively free posture. This also increases the usability of the teeth whitening device.

INDUSTRIAL APPLICABILITY

The present invention is valuable as it provides a usable teeth whitening device.

The invention claimed is:

1. A teeth whitening device comprising:
a generator configured to generate a teeth whitening fluid that whitens teeth and humidified gas; and
a mouthpiece including a supply port comprising a first supply port and a second supply port, the teeth whitening fluid being supplied through the first supply port, and the humidified gas generated by the generator being supplied through the second supply port, the second supply port being disposed separately from the first supply port such that the teeth whitening fluid and humidified gas are separated from each other until the teeth whitening fluid and humidified gas exit the mouthpiece.

2. The teeth whitening device according to claim 1, wherein the mouthpiece further includes a first supply passage configured to guide the teeth whitening fluid to the first supply port, and a second supply passage configured to guide the humidified gas to the second supply port, the second supply passage being formed separately from the first supply passage.

3. The teeth whitening device according to claim 1, wherein the first supply port and the second supply port are directed differently from each other.

4. The teeth whitening device according to claim 1, wherein the mouthpiece includes a curved element on which a guiding surface configured to guide the teeth whitening fluid is formed.

5. The teeth whitening device according to claim 4, wherein the supply port is opened in the guiding surface.

6. The teeth whitening device according to claim 1, further comprising a coupling part that couples the generator with the mouthpiece,
wherein the coupling part includes a supply passage that directly or indirectly communicates with the supply port.

* * * * *